(12) United States Patent
Farley et al.

(10) Patent No.: US 7,041,098 B2
(45) Date of Patent: May 9, 2006

(54) EXPANDABLE VEIN LIGATOR CATHETER AND METHOD OF USE

(75) Inventors: Brian E. Farley, Los Altos, CA (US); Dawn A. Henderson, Palo Alto, CA (US); Christopher S. Jones, Sunnyvale, CA (US); Mark P. Parker, San Jose, CA (US); Joseph M. Tartaglia, Morgan Hill, CA (US)

(73) Assignee: VNUS Medical Technologies, Inc., San Jose, CA (US)

( * ) Notice: Subject to any disclaimer, the term of this patent is extended or adjusted under 35 U.S.C. 154(b) by 29 days.

(21) Appl. No.: 10/162,057

(22) Filed: Jun. 3, 2002

(65) Prior Publication Data

US 2002/0147445 A1 Oct. 10, 2002

Related U.S. Application Data

(62) Division of application No. 09/497,099, filed on Feb. 3, 2000, now Pat. No. 6,398,780, and a division of application No. 08/958,766, filed on Oct. 26, 1997, now Pat. No. 6,165,172, which is a continuation of application No. 08/927,251, filed on Sep. 11, 1997, now Pat. No. 6,200,312.

(51) Int. Cl.
*A61B 18/18* (2006.01)

(52) U.S. Cl. .............................. 606/41; 606/49; 606/50; 607/99; 607/101; 607/105; 607/106; 607/113

(58) Field of Classification Search .................. 606/33, 606/45, 46, 47, 48, 49, 50, 41; 607/96, 98, 607/99, 116
See application file for complete search history.

(56) References Cited

U.S. PATENT DOCUMENTS 373,339 A 11/1887 Hamilton 659,409 A 10/1900 Mosher (Continued)

FOREIGN PATENT DOCUMENTS

DE 35 16830 A1 11/1986
EP 0 189 329 A2 7/1986

(Continued)

OTHER PUBLICATIONS

Aaron, et al, *The Medical Letter On Drugs And Therapeutics*, Jul. 12, 1968, pp. 53–55.

(Continued)

*Primary Examiner*—Rosiland Rollins
(74) *Attorney, Agent, or Firm*—Fulwider Patton LLP

(57) ABSTRACT

A catheter includes a plurality of primary leads to deliver energy for ligating a hollow anatomical structure. Each of the primary leads includes an electrode located at the working end of the catheter. Separation is maintained between the primary leads such that each primary lead can individually receive power of selected polarity. The primary leads are constructed to expand outwardly to place the electrodes into apposition with a hollow anatomical structure. High frequency energy can be applied from the leads to create a heating effect in the surrounding tissue of the anatomical structure. The diameter of the hollow anatomical structure is reduced by the heating effect, and the electrodes of the primary leads are moved closer to one another. Where the hollow anatomical structure is a vein, energy is applied until the diameter of the vein is reduced to the point where the vein is occluded. In one embodiment, a balloon is inflated to occlude the structure before the application of energy. Where the structure is a vein, the inflated balloon obstructs blood flow and facilitates the infusion of saline, medication, or a high-impedance fluid to the vein in order to reduce the occurrence of coagulation and to improve the heating of the vein by the catheter. The catheter can include a lumen to accommodate a guide wire or to allow fluid delivery.

11 Claims, 13 Drawing Sheets

U.S. PATENT DOCUMENTS

| | | |
|---|---|---|
| 833,759 A | 10/1906 | Sourwine |
| 985,865 A | 3/1911 | Turner, Jr. |
| 3,230,957 A | 1/1966 | Siefert |
| 3,301,258 A | 1/1967 | Werner et al. |
| 3,557,794 A | 1/1971 | Van Patten |
| 3,920,021 A | 11/1975 | Hiltebrandt |
| 4,016,886 A | 4/1977 | Doss et al. |
| 4,043,339 A | 8/1977 | Roseman |
| 4,119,102 A | 10/1978 | LeVeen |
| 4,154,246 A | 5/1979 | LeVeen |
| 4,312,364 A | 1/1982 | Convert et al. |
| 4,346,715 A | 8/1982 | Gammell |
| 4,522,205 A | 6/1985 | Taylor et al. |
| 4,643,186 A | 2/1987 | Rosen et al. |
| 4,660,571 A | 4/1987 | Hess et al. |
| 4,664,120 A | 5/1987 | Hess |
| 4,699,147 A | 10/1987 | Chilson et al. |
| 4,709,698 A | 12/1987 | Johnston et al. |
| 4,765,331 A | 8/1988 | Petruzzi et al. |
| 4,776,349 A | 10/1988 | Nashef et al. |
| 4,807,620 A | 2/1989 | Strul et al. |
| 4,823,812 A | 4/1989 | Eshel et al. |
| 4,945,912 A | 8/1990 | Langberg |
| 4,966,597 A | 10/1990 | Cosman |
| 4,976,711 A | 12/1990 | Parins et al. |
| 4,979,948 A | 12/1990 | Geddes et al. |
| 5,010,894 A | 4/1991 | Edhag |
| 5,057,107 A | 10/1991 | Parins et al. |
| 5,078,717 A | 1/1992 | Parins et al. |
| 5,117,828 A | 6/1992 | Metzger et al. |
| 5,122,137 A | 6/1992 | Lennox |
| 5,156,151 A | 10/1992 | Imran |
| 5,188,602 A | 2/1993 | Nichols |
| 5,215,103 A | 6/1993 | Desai |
| 5,255,678 A | 10/1993 | Deslauriers et al. |
| 5,263,493 A | 11/1993 | Avitall |
| 5,275,610 A | 1/1994 | Eberbach |
| 5,282,845 A | 2/1994 | Bush et al. |
| 5,293,869 A | 3/1994 | Edwards et al. |
| 5,383,917 A | 1/1995 | Desai et al. |
| 5,397,339 A | 3/1995 | Desai |
| 5,405,322 A | 4/1995 | Lennox et al. |
| 5,409,000 A | 4/1995 | Imran |
| 5,411,025 A | 5/1995 | Webster, Jr. |
| 5,423,815 A | 6/1995 | Fugo |
| 5,437,664 A | 8/1995 | Cohen et al. |
| 5,449,381 A | 9/1995 | Imran |
| 5,458,596 A | 10/1995 | Lax et al. |
| 5,465,717 A | 11/1995 | Imran et al. |
| 5,505,730 A | 4/1996 | Edwards |
| 5,514,130 A | 5/1996 | Baker |
| 5,545,161 A | 8/1996 | Imran |
| 5,556,396 A | 9/1996 | Cohen et al. |
| 5,709,224 A | 1/1998 | Behl et al. |
| 5,779,698 A * | 7/1998 | Clayman et al. ............... 606/39 |
| 5,810,804 A | 9/1998 | Gough et al. |
| 5,817,092 A | 10/1998 | Behl |
| 5,827,268 A | 10/1998 | Laufer |
| 5,863,290 A | 1/1999 | Gough et al. |
| 5,868,740 A | 2/1999 | LeVeen et al. |
| 5,916,235 A | 6/1999 | Guglielmi |
| 5,951,547 A | 9/1999 | Gough et al. |
| 5,964,753 A | 10/1999 | Edwards |
| 6,666,858 B1 * | 12/2003 | Lafontaine ................... 606/21 |

FOREIGN PATENT DOCUMENTS

| | | |
|---|---|---|
| EP | 0 629 382 A1 | 12/1994 |
| EP | 0 727 184 A1 | 8/1996 |
| EP | 0 738 501 A1 | 10/1996 |
| WO | WO 92/12681 | 8/1992 |
| WO | WO 93/21846 | 11/1993 |
| WO | WO 94/07446 | 4/1994 |
| WO | WO 94/21170 | 9/1994 |
| WO | WO 95/10236 | 4/1995 |
| WO | WO 95/10322 | 4/1995 |
| WO | WO 95/31142 | 11/1995 |
| WO | WO 96/32885 | 10/1996 |
| WO | WO 97/06739 | 2/1997 |
| WO | WO 97/17892 | 5/1997 |
| WO | WO 97/32532 | 9/1997 |
| WO | WO 98/18393 | 5/1998 |
| WO | WO 98/19613 | 5/1998 |

OTHER PUBLICATIONS

Watts, *Endovenous Diathermy Destruction Of Internal Saphenous,* British Medical Journal, Oct. 7, 1972, p. 53.

O'Reilly, *Endovenous Diathermy Sclerosis As A Unit Of The Armamentarioum For The Attack on Varicose Veins,* The Medical Journal of Australia, Jun. 1, 1974, at 900.

O'Reilly, *Edovenous Diathermy Sclerosis Of Varicose Veins,* The Australia, New Zealand Journal of Surgery, vol. 47, No. 3, Jun. 1977, pp. 393–395.

Brunelle, et al., *A Bipolar Electrode For Vascular Electrocoagulation With Alternating Current,* Technical Notes, Oct. 1980, vol. 137, pp. 239–240.

O'Reilly, *A Technique Of Diathermy Sclerosis Of Varicose Veins,* The Australia, New Zealand Journal of Surgery, vol. 51, No. 4, Aug. 1981, pp. 379–382.

Cragg, et al., *Endovascular Diathermic Vessel Occlusion,* Diagnostic Radiology, 144:303–308, Jul. 1982.

Ogawa, et al., *Electrothrombosis As A Treatment Of Cirsoid Angioma In The Face And Scalp And Varicosis Of The Leg,* Plastic And Reconstructive Surgery, Sep. 1982, pp. 310–318.

Gradman, *Venoscopic Obliteration Of Variceal Tributaries Using Monopolar Electrocautery,* Journal of Dermatology Surgery Oncology, 1994, 20, p. 482–485.

Money, *Endovascular Electroablation Of Peripheral Veins,* 22$^{nd}$ Annual Symposium, Current Critical Problems, New Horizons and Techniques in Vascular and Endovascular Surgery (Nov. 1995).

Inturri, *Pathophysiology Of Portal Hypertension,* Journal of Vascular Technology 19 (5–6):271–276, Sep.–Dec. 1995.

Crockett, et al., *Preliminary Experience With An Endovascular Catheter For Electrocoagulation of Peripheral Veins,* The Journal of Vascular Technology, Winter 1996, at 19–22.

* cited by examiner

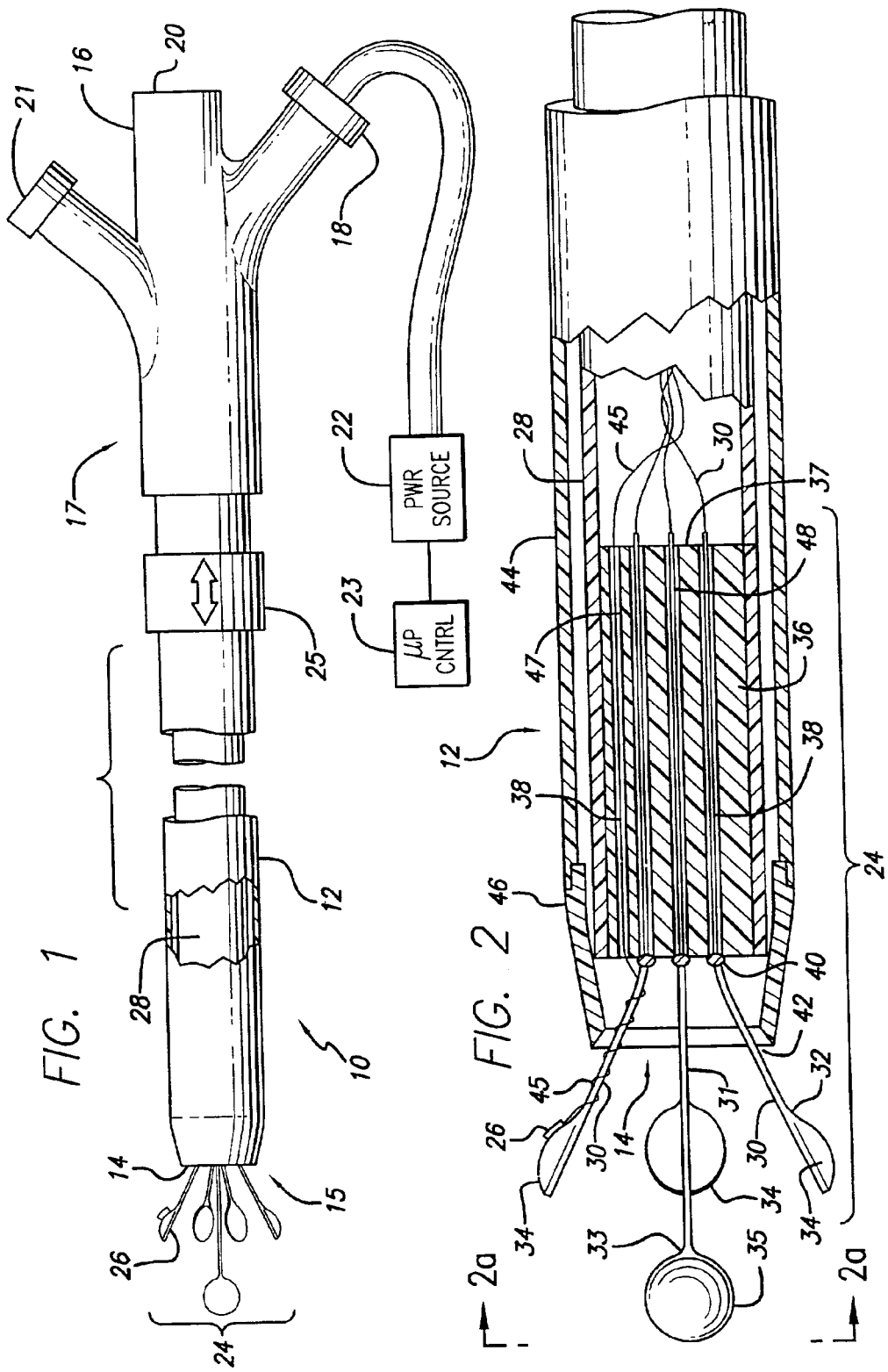

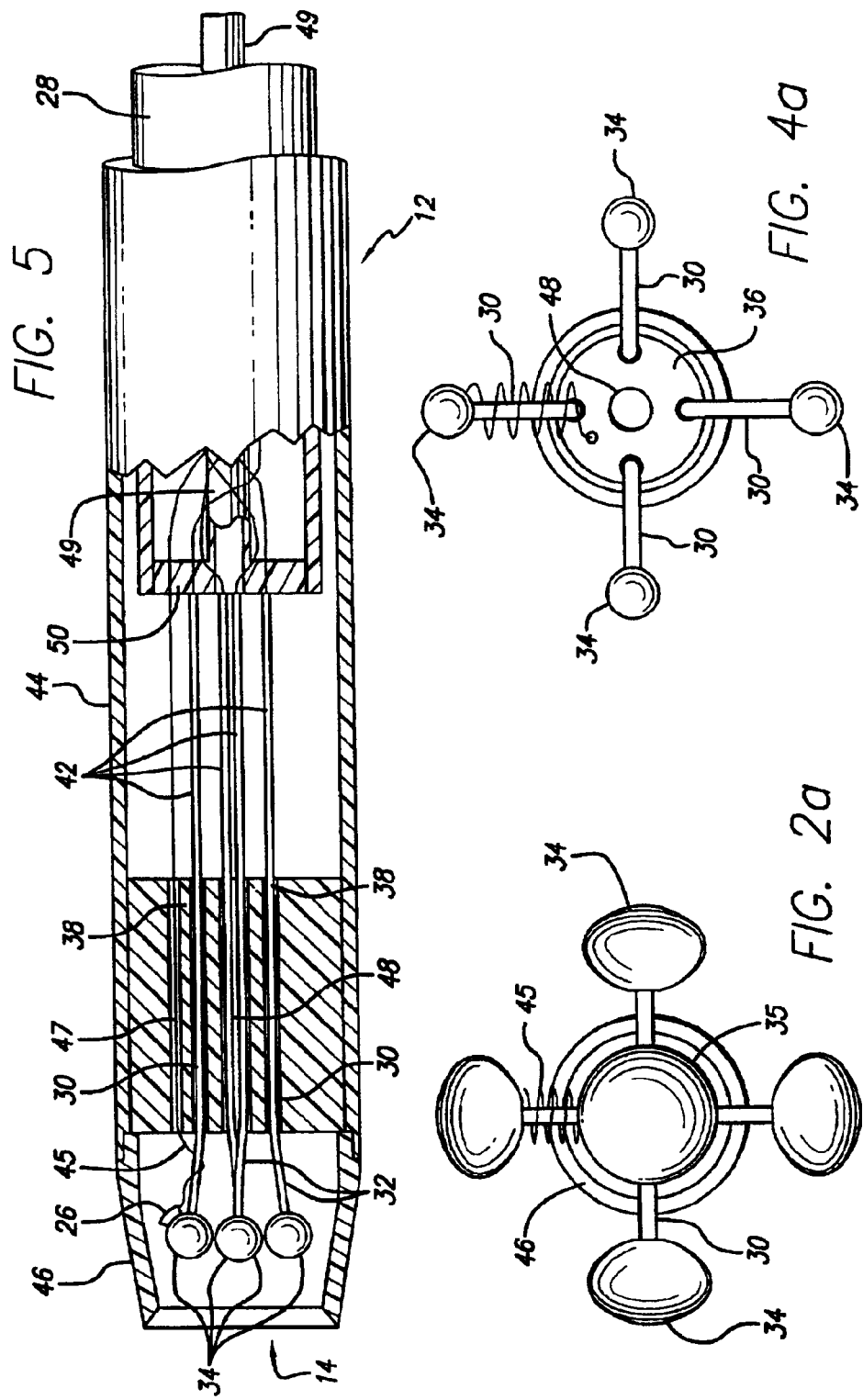

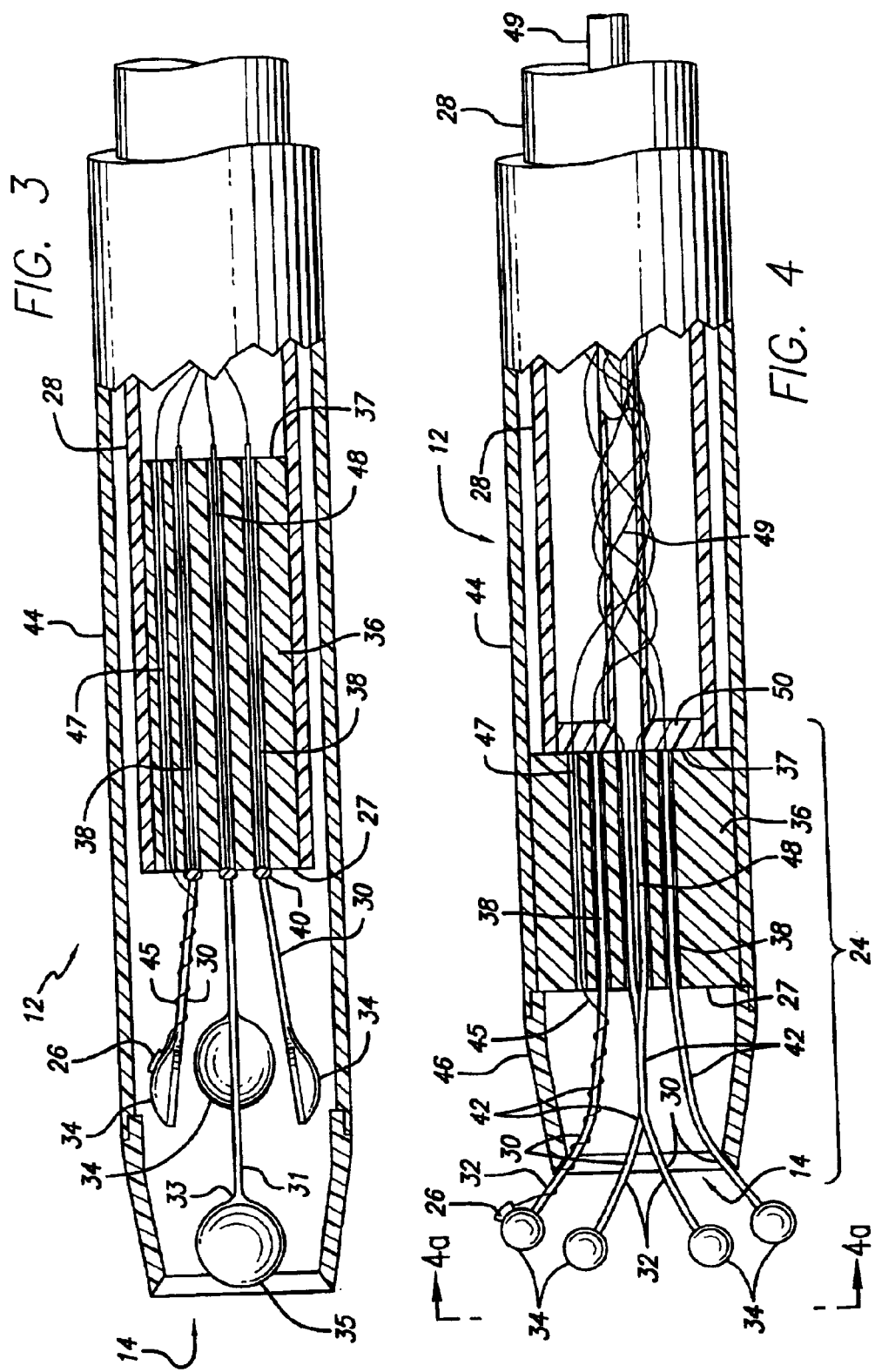

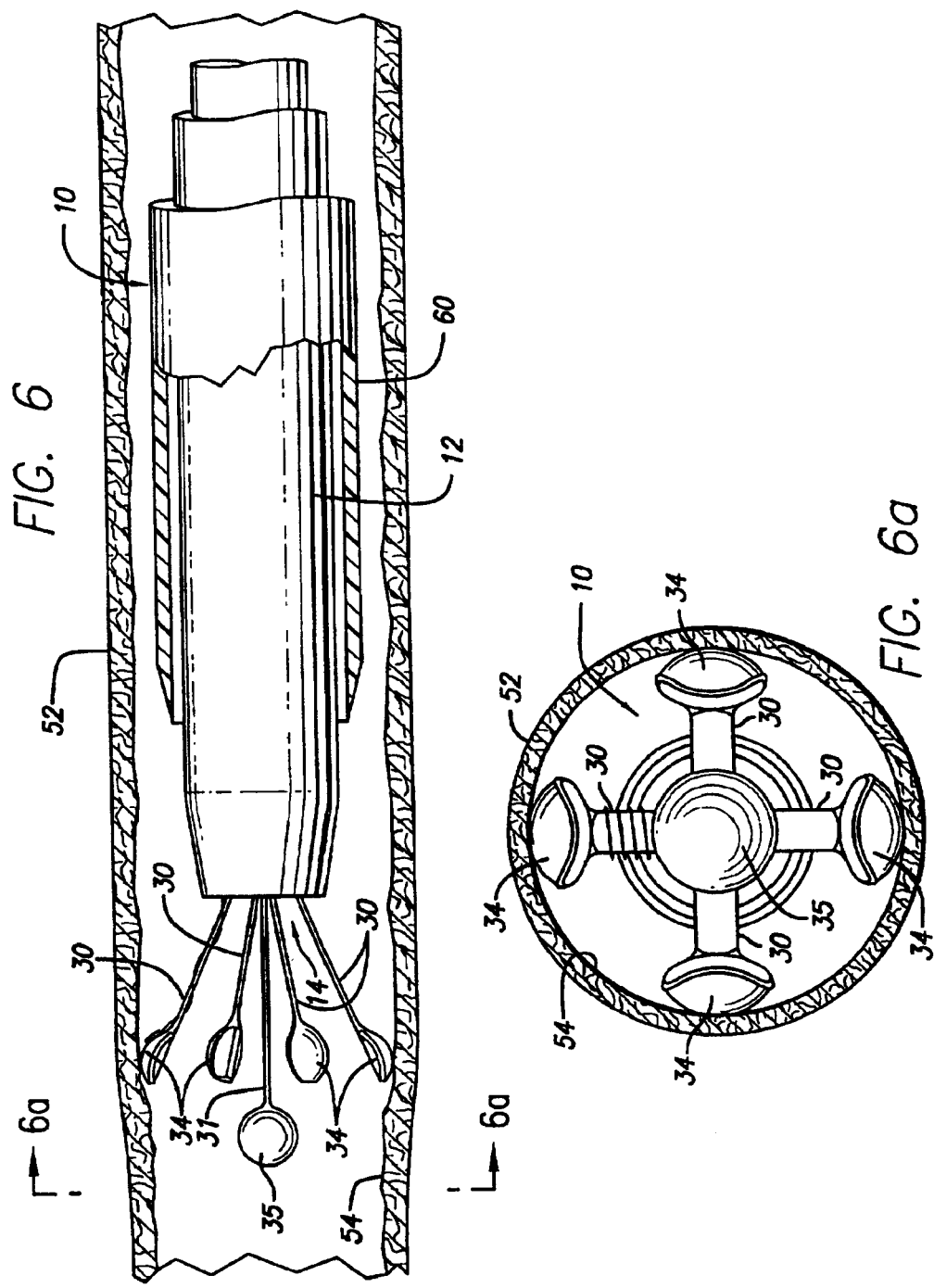

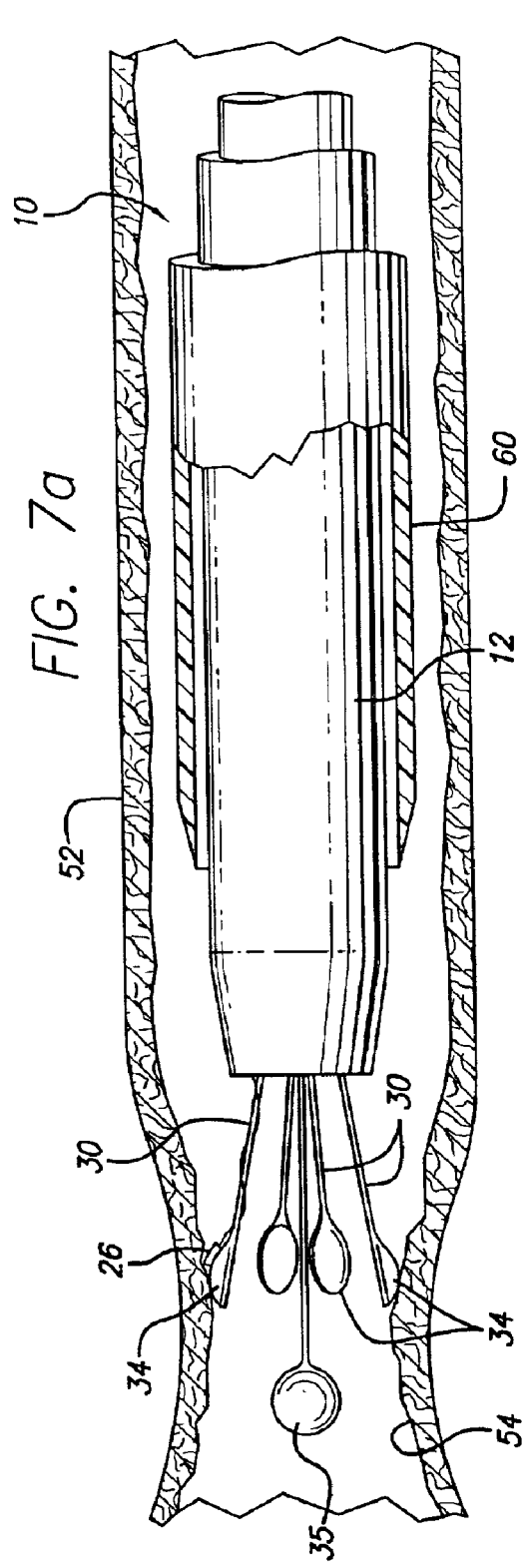
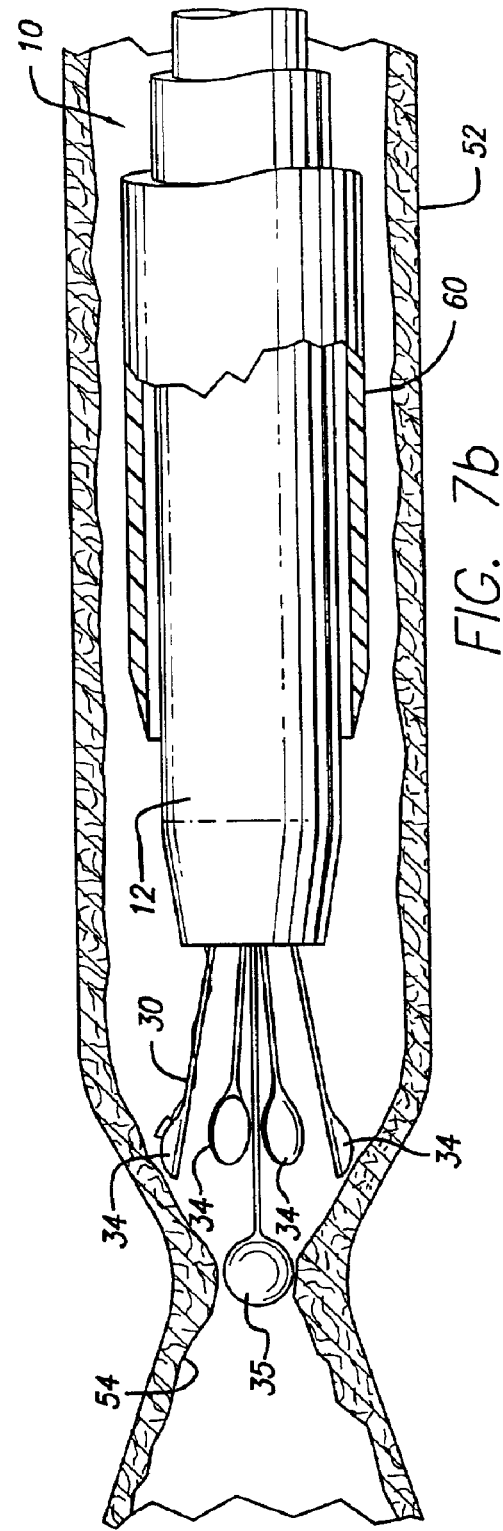

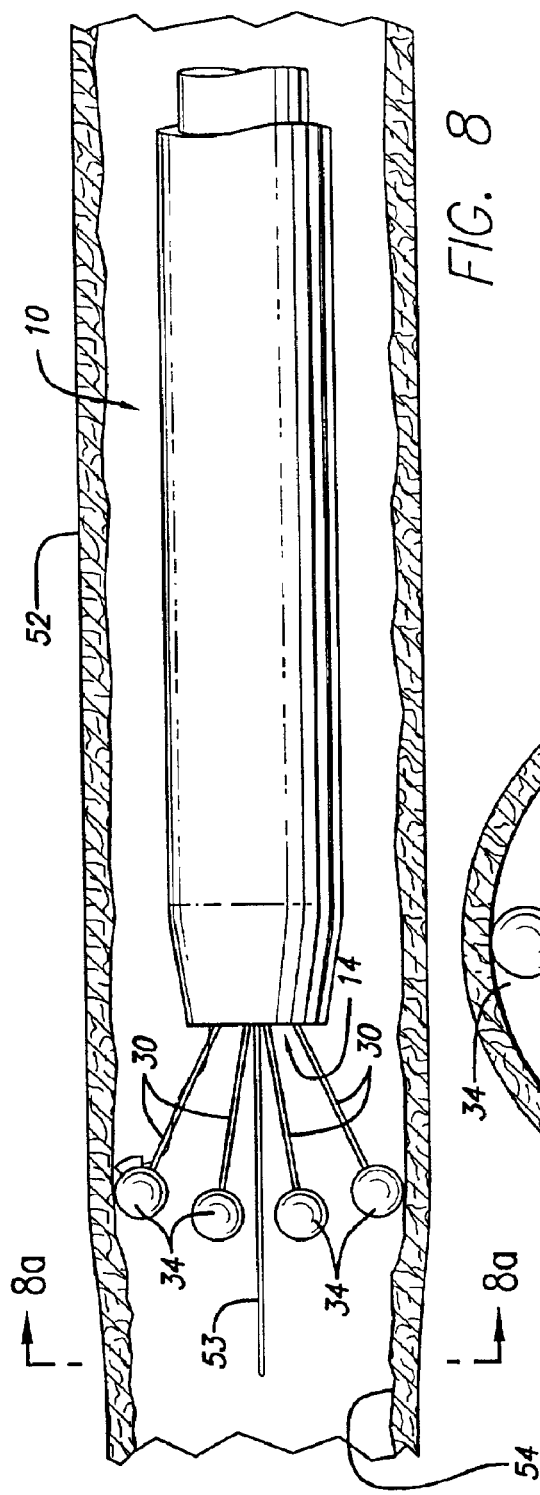
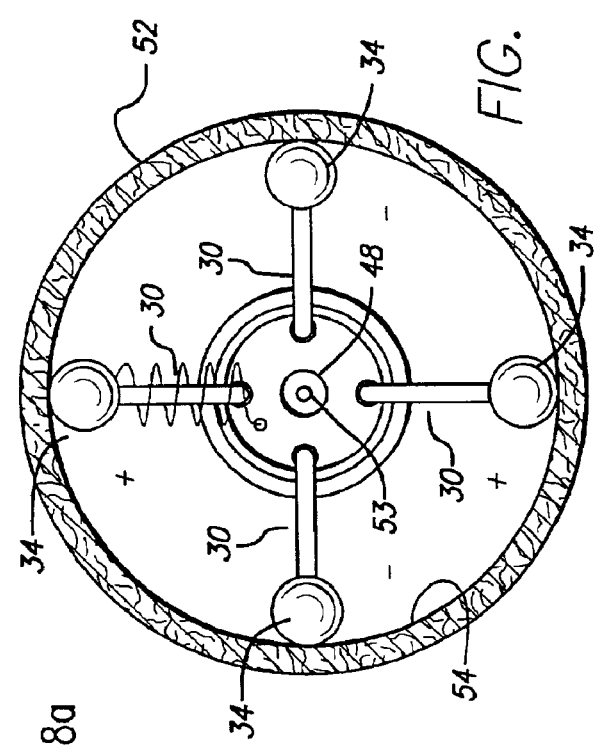

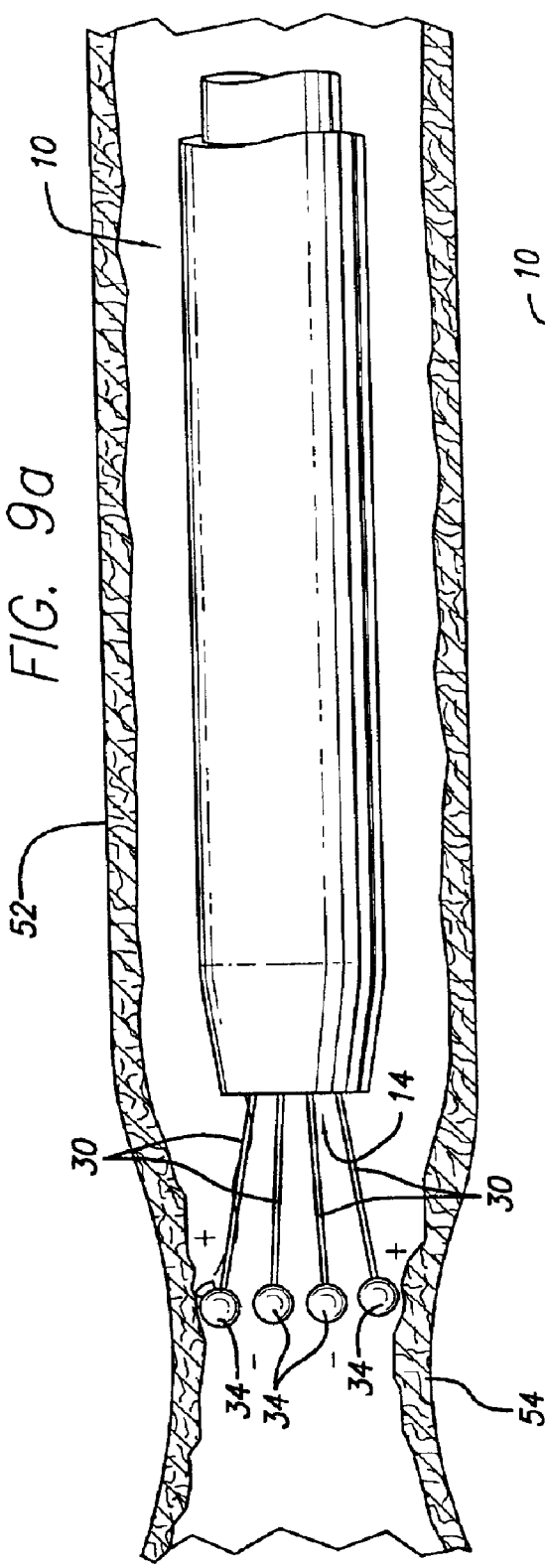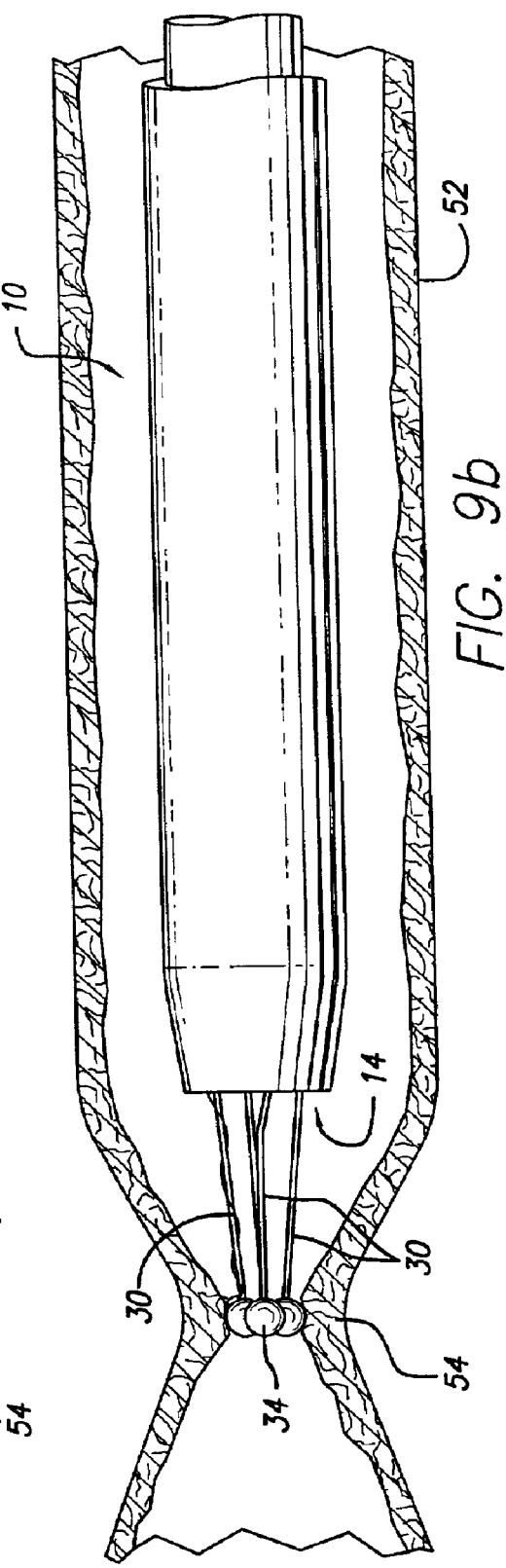

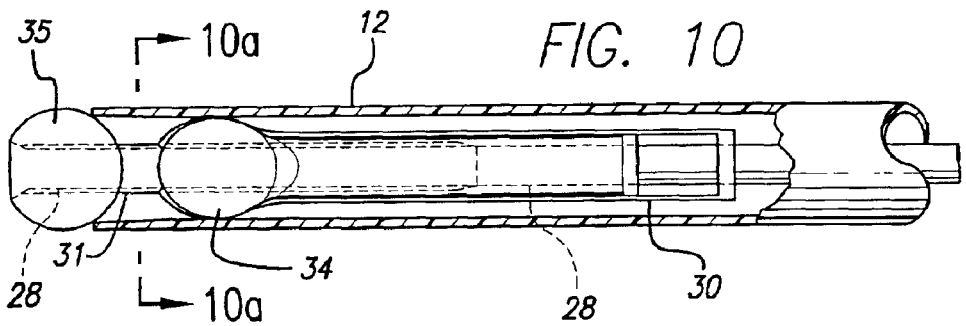
FIG. 10
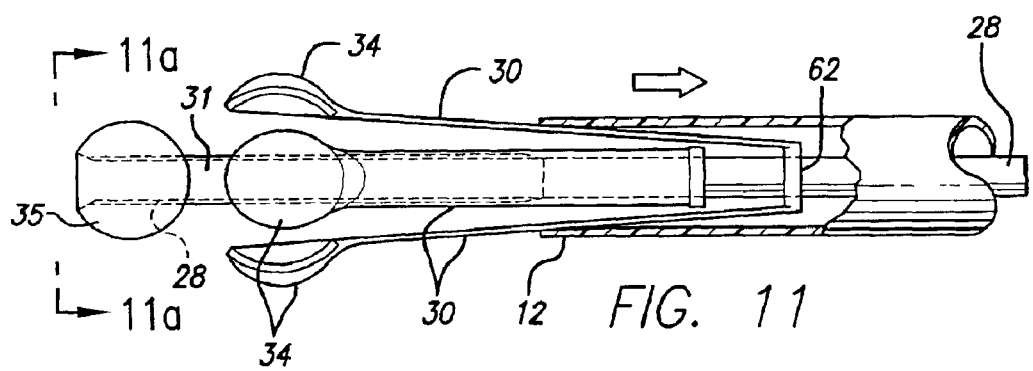
FIG. 11
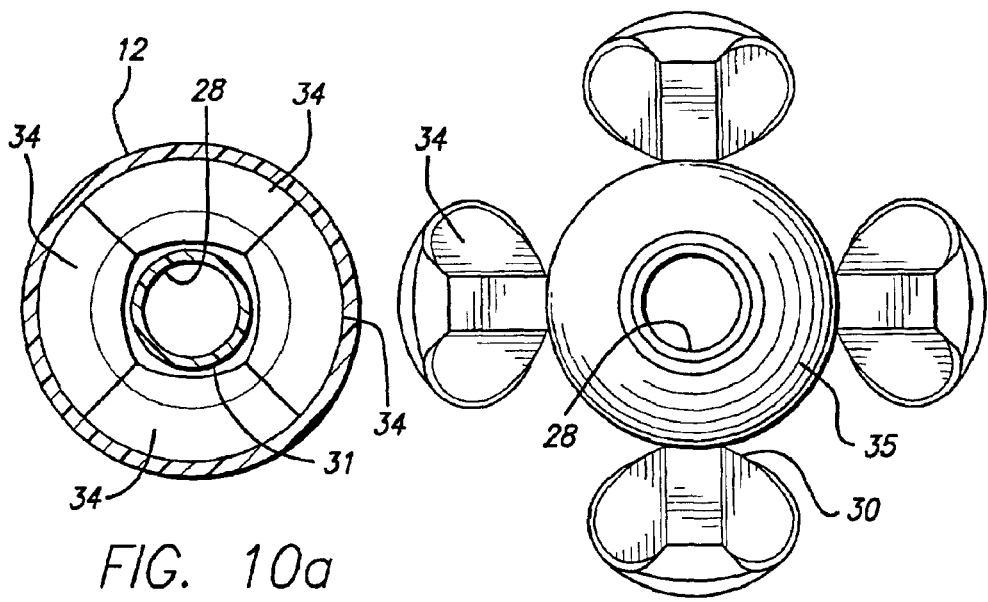
FIG. 10a
FIG. 11a

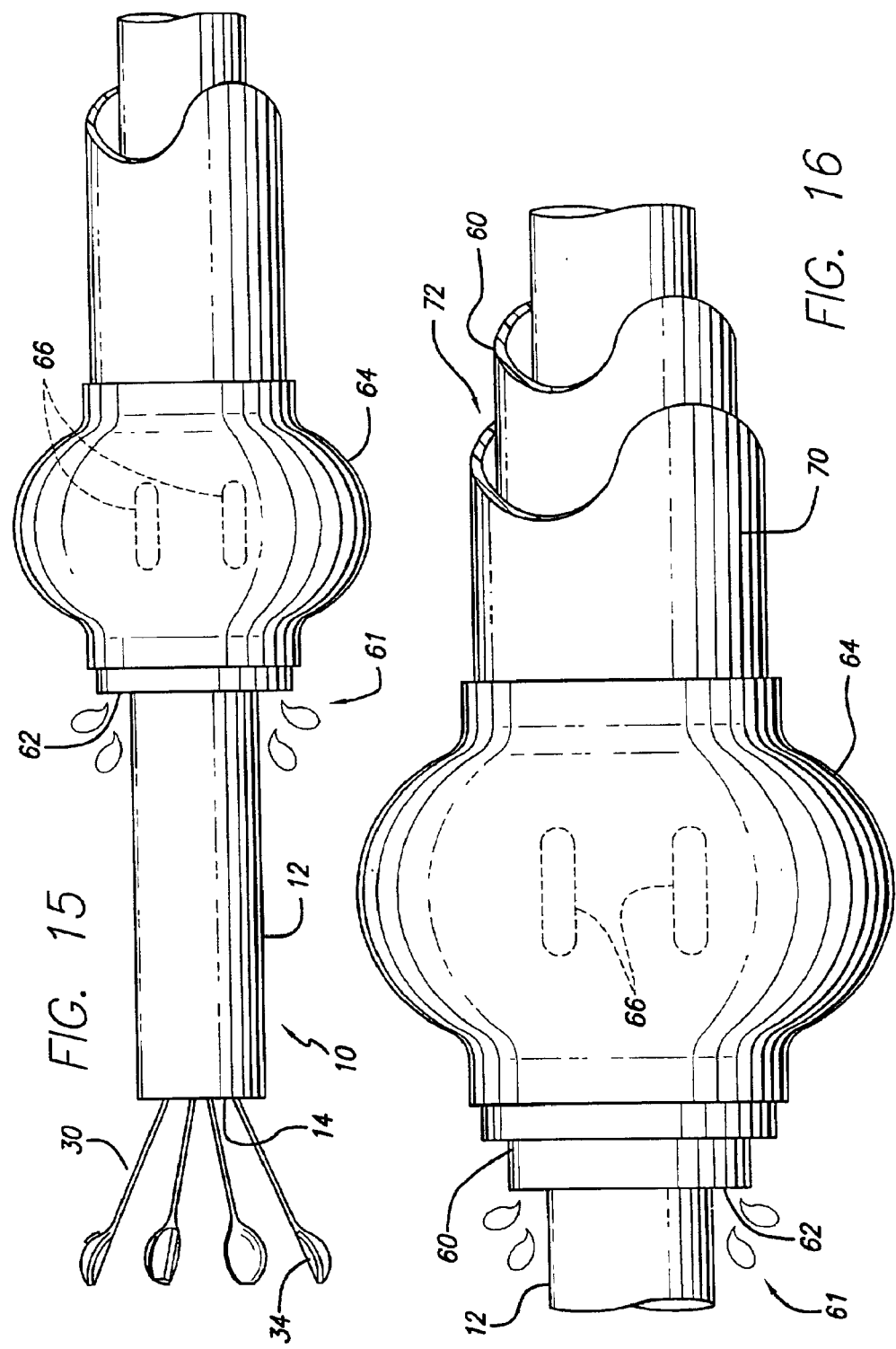

EXPANDABLE VEIN LIGATOR CATHETER AND METHOD OF USE

This is a division of co-pending application No. 09/497,099 filed on Feb. 3, 2000 Pat. No. 6,398,780, which is a division of Ser. No. 08/958,766 filed on Oct. 26, 1997 now U.S. Pat. No. 6,165,172 which is a Continuation-in-part of Ser. No. 08/927,251 filed on Sep. 11, 1997 now U.S. Pat. No. 6,200,312, the contents of which are incorporated by reference in their entireties.

BACKGROUND OF THE INVENTION

The invention relates generally to a method and apparatus for applying energy to shrink a hollow anatomical structure such as a vein, and more particularly, to a method and apparatus using an electrode device having multiple leads for applying said energy.

The human venous system of the lower limbs consists essentially of the superficial venous system and the deep venous system with perforating veins connecting the two systems. The superficial system includes the long or great saphenous vein and the short saphenous vein. The deep venous system includes the anterior and posterior tibial veins which unite to form the popliteal vein, which in turn becomes the femoral vein when joined by the short saphenous vein.

The venous system contains numerous one-way valves for directing blood flow back to the heart. Venous valves are usually bicuspid valves, with each cusp forming a sack or reservoir for blood which, under retrograde blood pressure, forces the free surfaces of the cusps together to prevent retrograde flow of the blood and allows only antegrade blood flow to the heart. When an incompetent valve is in the flow path, the valve is unable to close because the cusps do not form a proper seal and retrograde flow of the blood cannot be stopped. When a venous valve fails, increased strain and pressure occur within the lower venous sections and overlying tissues, sometimes leading to additional valvular failure. Two venous conditions which often result from valve failure are varicose veins and more symptomatic chronic venous insufficiency.

The varicose vein condition includes dilation and tortuosity of the superficial veins of the lower limbs, resulting in unsightly discoloration, pain, swelling, and possibly ulceration. Varicose veins often involve incompetence of one or more venous valves, which allow reflux of blood within the superficial system. This can also worsen deep venous reflux and perforator reflux. Current treatments of vein insufficiency include surgical procedures such as vein stripping, ligation, and occasionally, vein-segment transplant.

Ligation involves the cauterization or coagulation of vascular lumina using electrical energy applied through an electrode device. An electrode device is introduced into the vein lumen and positioned so that it contacts the vein wall. Once properly positioned, RF energy is applied to the electrode device thereby causing the vein wall to shrink in cross-sectional diameter. A reduction in cross-sectional diameter, as for example from 5 mm (0.2 in) to 1 mm (0.04 in), significantly reduces the flow of blood through the vein and results in an effective ligation. Though not required for effective ligation, the vein wall may completely collapse thereby resulting in a full-lumen obstruction that blocks the flow of blood through the vein.

One apparatus for performing venous ligation includes a tubular shaft having an electrode device attached at the distal tip. Running through the shaft, from the distal end to the proximal end, are electrical leads. At the proximal end of the shaft, the leads terminate at an electrical connector, while at the distal end of the shaft the leads are connected to the electrode device. The electrical connector provides the interface between the leads and a power source, typically an RF generator. The RF generator operates under the guidance of a control device, usually a microprocessor.

The ligation apparatus may be operated in either a monopolar and bipolar configuration. In the monopolar configuration, the electrode device consists of an electrode that is either positively or negatively charged. A return path for the current passing through the electrode is provided externally from the body, as for example by placing the patient in physical contact with a large low-impedance pad The current flows from the ligation device to the low impedance pad. In a bipolar configuration, the electrode device consists of a pair of oppositely charged electrodes separated by a dielectric material. Accordingly, in the bipolar mode, the return path for current is provided by the electrode device itself. The current flows from one electrode, through the tissue, and returns by way of the oppositely charged electrode.

To protect against tissue damage, i.e., charring, due to cauterization caused by overheating, a temperature sensing device is attached to the electrode device. The temperature sensing device may be a thermocouple that monitors the temperature of the venous tissue. The thermocouple interfaces with the RF generator and the controller through the shaft and provides electrical signals to the controller which monitors the temperature and adjusts the energy applied to the tissue, through the electrode device, accordingly.

The overall effectiveness of a ligation apparatus is largely dependent on the electrode device contained within the apparatus. Monopolar and bipolar electrode devices that comprise solid devices having a fixed shape and size limit the effectiveness of the ligating apparatus for several reasons. Firstly, a fixed-size electrode device typically contacts the vein wall at only one point on the circumference or inner diameter of the vein wall. As a result, the application of RF energy is highly concentrated within the contacting venous tissue, while the flow of RF current through the remainder of the venous tissue is disproportionately weak. Accordingly, the regions of the vein wall near the point of contact collapse at a faster rate then other regions of the vein wall, resulting in non-uniform shrinkage of the vein lumen. Furthermore, the overall strength of the occlusion may be inadequate and the lumen may eventually reopen. To avoid an inadequate occlusion RF energy must be applied for an extended period of time. Application of RF energy as such increases the temperature of the blood and usually results in a significant amount of heat-induced coagulum forming on the electrode and in the vein which is not desirable.

Secondly, the effectiveness of a ligating apparatus having a fixed electrode device is limited to certain sized veins. An attempt to ligate a vein having a diameter that is substantially greater than the electrode device can result in not only non-uniform shrinkage of the vein wall as just described, but also insufficient shrinkage of the vein. The greater the diameter of the vein relative to the diameter of the electrode device, the weaker the energy applied to the vein wall at points distant from the point of contact. Accordingly the vein wall is likely to not completely collapse prior to the venous tissue becoming over cauterized at the point of electrode contact. While coagulation as such may initially occlude the vein, such occlusion may only be temporary in that the coagulated blood may eventually dissolve and the vein partially open. One solution for this inadequacy is an apparatus having interchangeable electrode devices with various diameters. Such a solution, however, is both economically inefficient and tedious to use.

Hence those skilled in the art have recognized a need for an expandable electrode device and a method capable of evenly distributing RF energy along a circumferential band of a vein wall where the vein wall is greater in diameter than the electrode device, and thereby provide more predictable and effective occlusion of veins while minimizing the formation of heat-induced coagulum. The invention fulfills these needs and others.

SUMMARY OF THE INVENTION

Briefly, and in general terms, the present invention provides an apparatus and method for applying energy along a generally circumferential band of a vein wall. The application of energy as such results in a more uniform and predictable shrinkage of the vein wall.

In one aspect of the invention, an apparatus for delivering energy to ligate an anatomical structure comprises a catheter having a sheath, a working end, and an opening formed at the working end of the catheter; an inner member disposed within the sheath such that the inner member and the sheath are capable of being moved relative to one another; a plurality of leads, each lead having a distal end, the plurality of leads being coupled with the inner member such that the distal ends of the plurality of leads extend out of the opening at the working end of the catheter when the position of the sheath changes in one direction relative to the inner member, each lead being formed to move the distal end away from a longitudinal axis defined by the sheath when the plurality of leads are extended out the opening; wherein the distal ends of the leads are configured to deliver energy to the anatomical structure.

In another aspect of the invention, the apparatus includes a secondary lead having a secondary distal end. The secondary lead is coupled with the inner member such that the distal end of the secondary lead is extended out of the opening at the working end of the catheter when the position of the inner member changes in one direction relative to the sheath.

In another aspect of the invention, the distal ends of the leads are electrically connected to a power source such that the polarity of each lead can be switched. Where there is a secondary lead electrode, the plurality of leads can be connected to the power source such that the polarity of the leads can be changed independently of the polarity of the secondary lead.

In another aspect, the leads include primary leads which generally surround the secondary lead at the working end of the catheter. The distal ends of the primary leads are located between the distal end of the secondary lead and the inner member.

In yet another aspect, the invention comprises a method of applying energy to a hollow anatomical structure from within the structure. The method includes the step of introducing a catheter into the anatomical structure; the catheter having a working end and a plurality of leads, each lead having a distal end, and each lead being connected to a power source. The method also includes the step of expanding the leads outwardly through the distal orifice and expanding the leads until each electrode contacts the anatomical structure. The method further includes the step of applying energy to the anatomical structure from the distal end of the leads, until the anatomical structure collapses.

In another aspect of the invention, the method also includes the step of introducing a catheter into the anatomical structure where the catheter has a secondary lead that has a distal portion that is greater in length than the primary-lead distal portions and is generally surrounded by the primary leads. The secondary lead also has an electrode at the distal end. The method also includes the steps of extending the primary and secondary leads through the orifice until each primary-lead electrode contacts the anatomical structure, and controlling the power source so that adjacent primary leads are of opposite polarity while maintaining the secondary lead so that it is electrically neutral. Upon collapse of the anatomical structure around the primary leads, the polarity of the primary leads is switched so that they are all of the same polarity. Upon switching the polarity of the primary leads so that they are of the same polarity, controlling the power source so that the secondary lead is of opposite polarity relative to the primary leads. The method, in a further aspect, comprises the step of moving the catheter in the anatomical structure while continuing to apply energy to the anatomical structure to lengthen the area of ligation.

In another aspect of the invention, external compression is used to initially force the wall of the vein to collapse toward the catheter. The application of energy molds the vein to durably assume the collapsed state initially achieved mechanically by the external compression. A tourniquet can be used to externally compress or flatten the anatomical structure and initially reduce the diameter of the hollow anatomical structure. The pressure applied by the tourniquet can exsanguinate blood from the venous treatment site, and pre-shape the vein in preparation to be molded to a ligated state. An ultrasound window formed in the tourniquet can be used to facilitate ultrasound imaging of the anatomical structure being treated through the window.

In yet another aspect of the invention, a balloon is provided to occlude the vein before the application of energy, such that the need for an external compression by a tourniquet is not required to stop blood flow. This also allows the vein to be occluded even for the deep veins where a compressive tourniquet may not be able to compress the vein to occlusion.

In yet another aspect of the invention, a flexible covering, relatively impermeable to fluid, spans the area between the leads along the circumference of the catheter when the leads are extended out, such that the webbed covering blocks blood flow within the vein.

In yet another aspect of the invention, a flexible balloon-like covering is located on the catheter, having openings to the concave side and a convex side facing the working end of the catheter. The covering fills with blood and expands. When the covering balloons out to the diameter of the vein, blood flow is stopped.

In yet another aspect of the invention, mechanically blocking blood flow with the catheter is combined with infusion of a high-impedance fluid. The fluid may also be an anticoagulant. The fluid displaces any remaining blood from the venous treatment site and prevents energy from being dissipated away from the vein which is in apposition with the electrodes.

These and other aspects and advantages of the present invention will become apparent from the following more detailed description, when taken in conjunction with the accompanying drawings which illustrate, by way of example, embodiments of the invention.

BRIEF DESCRIPTION OF THE DRAWINGS

FIG. 1 is a diagram of an energy application system with a partial cutaway view of a catheter showing both the working end and the connecting end and incorporating a preferred embodiment of the present invention;

FIG. 2 is a cross-sectional view of the working end of a first embodiment of a catheter in accordance with the invention depicting the electrodes in a fully extended position;

FIG. 2a is an end view of the working end of the first embodiment of the catheter taken along line 2a—2a of FIG. 2;

FIG. 3 is a cross-sectional view of the working end of the first embodiment depicting the electrodes in a fully retracted position;

FIG. 4 is a cross-sectional view of the working end of a second catheter in accordance with principles of the invention depicting the electrodes in a fully extended position;

FIG. 4a is an end view of the second embodiment of the invention taken along line 4a—4a of FIG. 4;

FIG. 5 is a cross-sectional view of the working end of the second embodiment of the catheter of FIG. 4 depicting the electrodes in a fully retracted position;

FIG. 6 is a cross-sectional view of an anatomical structure containing the catheter of FIG. 2 with the electrodes in apposition with the anatomical structure;

FIG. 6a is an end view of the anatomical structure containing the catheter taken along line 6a—6a of FIG. 6;

FIGS. 7a through 7c are cross-sectional views of the anatomical structure containing a catheter in accordance with the first embodiment of the invention and depicting the anatomical structure at various stages of ligation;

FIG. 8 is a cross-sectional view of an anatomical structure containing a catheter in accordance with the second embodiment of the invention as depicted in FIG. 4;

FIG. 8a is an end view of the anatomical structure containing the catheter taken along line 8a—8a of FIG. 8; and FIGS. 9a and 9b are cross-sectional views of the anatomical structure containing the catheter in accordance with the second embodiment of the invention and depicting the anatomical structure at various stages of ligation;

FIG. 10 is a cross-sectional view of the working end of a third embodiment of a catheter in accordance with the invention depicting the electrodes in a fully extended position;

FIG. 10a is an end view of the working end of the third embodiment of the catheter taken along line 10a—10a of FIG. 10;

FIG. 11 is a cross-sectional view of the working end of the third embodiment depicting the electrodes in a fully retracted position;

FIG. 15 is a side view of another embodiment of an electrode catheter having a balloon and a coaxial fluid channel;

FIG. 16 is a partial cross-sectional view of the balloon and catheter of FIG. 15;

DETAILED DESCRIPTION OF THE EMBODIMENTS

Figure 7C:
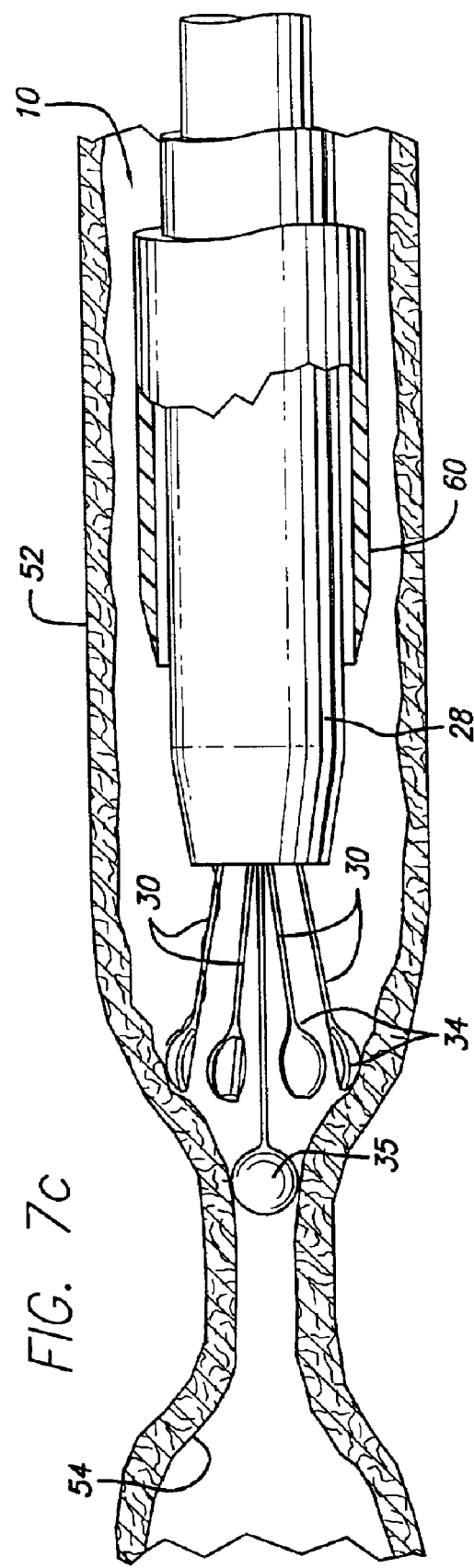

Turning now to the drawings with more particularity wherein like reference numerals indicate like or corresponding elements among the figures, shown in FIG. 1 is a catheter 10 for applying energy to an anatomical structure such as a vein. The catheter 10 includes an outer sheath 12 having a distal orifice 14 at its working end 15. The connector end 17 of the outer sheath 12 is attached to a handle 16 that includes an electrical connector 18 for interfacing with a power source 22, typically an RF generator, and a microprocessor controller 23. The power source 22 and microprocessor 23 are usually contained in one unit. The controller 23 controls the power source 22 in response to external commands and data from a sensor, such as a thermocouple, located at an intraluminal venous treatment site. In another embodiment, the user can select a constant power output so that automated temperature control is not present and the user can manually adjust the power output in view of the temperature on a display readout. The catheter 10 includes an expandable electrode device 24 (partially shown) that moves in and out of the outer sheath 12 by way of the distal orifice 14. The electrode device includes a plurality of electrodes which can be expanded by moving the electrodes within the shaft, or by moving the outer shaft relative to the electrodes. Although FIG. 1 illustrates a plurality of electrodes surrounding a single central electrode, different electrode configurations will be described for the catheter.

Contained within the outer sheath 12 is an inner sheath 28 or inner member. A fluid port 21 communicates with the interior of the outer sheath 12. The catheter 10 can be periodically flushed out with saline through the port 21. The flushing fluid can travel between the outer sheath and the inner sheath. The port also allows for the delivery of drug therapies. Flushing out the catheter prevents the buildup of biological fluid, such as blood, within the catheter 10. The treatment area of the hollow anatomical structure such as a vein can be flushed with a fluid such as saline, or a dielectric fluid, in order to evacuate blood from the treatment area of the vein so as to prevent the formation of coagulum or thrombosis. The use of a dielectric fluid can minimize unintended heating effects away from the treatment area. The dielectric fluid prevents the current of RF energy from flowing away from the vein wall.

In one embodiment, the catheter 10 includes a lumen which begins at the distal tip of the outer sheath 12 and runs substantially along the axis of the outer sheath 12 before terminating at the guide-wire port 20 of the handle 16. A guide wire can be introduced through the lumen of the catheter 10 for use in guiding the catheter to the desired treatment site. Where the catheter is sized to treat smaller veins, the outer diameter of the catheter may not allow for a fluid flush between the outer sheath 12 and the inner sheath 28. However, a fluid flush can be introduced through the lumen for the guide wire in such an embodiment.

Referring now to FIGS. 2, 2a, 3, 4, 4a and 5, the outer sheath 12 includes a shell 44 and a tip portion 46. To provide an atraumatic tip for the catheter 10 as it is manipulated through the vein, the tip 46 is preferably tapered inward at its distal end or is "nosecone" shaped. The tip 46, however, can have other shapes that facilitate tracking of the catheter 10 over a guide wire and through the bends in the venous vascular system. The nosecone-shaped tip 46 can, for example, be fabricated from a polymer having a soft durometer, such as 70 Shore A. The shell 44 comprises a biocompatible material having a low coefficient of friction. In one configuration, the outer sheath 12 is sized to fit within a venous lumen and for example may be between 5 and 9 French, which corresponds to a diameter of between 1.7 mm (0.07 in) and 3.0 mm (1.2 in), or other sizes as appropriate.

The electrode device 24 contains a number of leads, including insulated primary leads 30 and, in some embodiments, a secondary lead 31. Preferably, the leads are connected to the power source 22 (FIG. 1) such that the polarity of the leads may be switched as desired. Alternately, a microprocessor controller can be used to switch the polarity, as well as control other characteristics of the power for the electrode device. Thus the electrode device can operate in either a bipolar or a monopolar configuration. When adjacent primary leads 30 have opposite polarity the electrode device 24 operates as a bipolar electrode device. When the primary leads 30 are commonly charged the electrode device 24 can operate as a monopolar electrode device. When the primary leads 30 are commonly charged, and a secondary lead 31 has an opposite polarity, the electrode device 24 operates as a bipolar electrode device. The embodiment of the invention shown in FIGS. 2 and 3 depict an electrode device 24 having four primary leads 30 and a secondary lead 31, while the embodiment of the invention shown in FIGS. 4 and 5 depict an electrode device 24 having only four primary leads. The invention is not limited to four primary leads 30; more or fewer leads may be used in either embodiment. The number of leads can be dependent on the size or diameter of the hollow anatomical structure to be treated. The apposed electrodes should be kept within a certain distance of one another. Larger vessels may require more primary leads to ensure proper current density and proper heat distribution.

The insulation on each of the leads 30, 31 may be removed at the distal end 32, 33 to expose the conductive wire. In the first configuration as shown in FIGS. 2, 2a, and 3, the electrode 34 has a hemispherical shape. In a second configuration, the electrode can have either a generally spherical shape or a spoon shape. As shown in FIGS. 4, 4a and 5, the electrodes have a spoon shape which can be combined to form a sphere or other shape so as to minimize its profile when the vein collapses. The electrodes 34 are either integrally formed at the distal end 32, soldered, or otherwise formed to the distal end of each primary lead 30. It is to be understood that when the distal end 32 is referred to as acting as an electrode, this is not limited to where the electrode 34 is integrally formed at the distal end 32. For example, the distal end can apply energy to the surrounding tissue where there is an electrode integrally formed at the distal end, or where an electrode is separately soldered to the distal end, or where there is another energy delivery device located at the distal end. The electrode 34 typically has a diameter greater than the diameter of the primary lead 30. For example, the primary lead 30 may have a diameter ranging from 0.18 mm (0.007 in.) to 0.28 mm (0.011 in.), while the electrode 34 has a diameter of 0.36 mm (0.014 in.) to 0.51 mm (0.020 in.). The primary leads 30 and the electrodes 34 are preferably made from a biologically-compatible material such as stainless steel. The insulation surrounding the primary leads 30 generally has a thickness of between 0.03 mm (0.001 in.) and 0.06 mm (0.0025 in.), resulting in a combined lead-insulation diameter of between 0.23 mm (0.009 in.) and 0.41 mm (0.016 in.). In an alternate configuration, as shown in FIGS. 2 and 3, each primary lead 30 is strip-shaped with a width from 0.76 mm (0.03 in.) to 1.0 mm (0.04 in) and a thickness of approximately 0.13 mm (0.005 in.), while the secondary lead 31 is typically tubular-shaped. It should be noted that these dimensions are provided for illustrative purposes, and not by way of limitation. A hemispherical electrode 34 is shaped at the distal end, as for example, by sanding down a sixteenth-inch (1.6 mm) diameter sphere which is soldered to the distal end 32 of the primary lead 30. The electrodes can also be constructed by stamping the desired shape or configuration from the conductive lead. The electrode is integral with the lead, and the remainder of the lead is insulated. The distal end 33 of the secondary lead 31 preferably includes a generally spherically-shaped electrode 35.

An alignment device 36 arranges the leads 30, 31 such that they are mounted to the catheter at only their proximal ends and so that separation is maintained between the leads within, and distal to the alignment device. The leads can form cantilevers when mounted on the alignment device. A preferred configuration of the alignment device 36 includes a plurality of off-center, axially-aligned lumina 38 which are substantially symmetrically positioned relative to the axis of the alignment device 36. The alignment device 36 is formed, for example, by extruding the plurality of axially-aligned lumina 38 through a solid cylinder composed of a dielectric material, such as polyamide. Each lead 30 passes through an individual off-center lumen 38 and exits out the rear of the alignment device 36. The alignment device 36 may further include a central lumen 48 that may be aligned with the axis. In some embodiments the central lumen 48 is used for accepting a guide wire or for the delivery or perfusion of medicant and cooling solution to the treatment area during application of RF energy. In other embodiments, the central lumen 48 may be used for the secondary lead 31. The alignment device 36 may also further include an auxiliary lumen 47 for additional leads, such as the leads of a thermocouple used as a temperature sensor. The alignment device 36 comprises a dielectric material to prevent or minimize any coupling effect the leads 30, 31 may have with each other and, if present, the guide wire. The length of the alignment device is, for example, 12.5 mm (0.5 in.) to 19.0 mm (0.75 in.) in one embodiment. However, these dimensions are provided for purposes of illustration and not by way of limitation.

In the embodiment of the invention shown in FIGS. 2, 2a and 3, the inner sheath 28 is attached to the alignment device 36 and extends beyond the rear 37 of the alignment device. Preferably, the inner sheath 28 completely surrounds the exterior wall of the alignment device 36 and is mounted to it by adhesive or press fit or in other manner such that it remains in a fixed position relative to the inner sheath. The inner sheath and alignment device can act as an inner member relative to the outer sheath. The inner sheath 28 comprises a biocompatible material with a low coefficient of friction. The inner sheath 28 provides a pathway for the interconnection between the leads 30, 31 and the electrical connector 18 (FIG. 1). This interconnection may occur in any of several ways. The leads 30, 31 themselves may be continuous and run the entire length of the inner sheath 28. In the alternative (not shown), the positively charged leads 30, 31 may couple with a common positively charged conductor housed in the inner sheath 28. Likewise, the negatively charged leads 30, 31 may couple with a common negative conductor. Preferably, the leads 30, 31 are connected to a conductor that allows for the polarity of the leads to be switched. The conductor may comprise, for example, a 36 gauge copper lead with a polyurethane coating. The coupling may occur at any point within the inner sheath 28. To reduce the amount of wire contained in the catheter, it is advantageous to couple the leads 30, 31 at the point where the leads exit the rear 37 of the alignment device 36. To add further stability to the electrode device 24, it is preferred that bonding material 40 surround the leads 30, 31 at the front end of the alignment device 36. In this embodiment, the leads 30, 31 exit through the distal orifice 14 as the outer sheath 12 is retracted backwards over the alignment device 36. The inwardly tapered tip 46 impedes the retracting movement of the outer sheath 12 to prevent the exposure of the alignment device 36.

FIG. 3 shows the leads 30 and 31 in the retracted position where all leads are within the nosecone-shaped tip portion 46 and the outer shell 44. The alignment device 36 has been moved relative to the outer shell 44. The soft nosecone provides an atraumatic tip for when the catheter is maneuvered through the tortuous venous system. The electrode at the distal end of the secondary lead 31 can be sized to approximately the same size as the opening formed in the nosecone 46. The nosecone forms a closed atraumatic tip together with the electrode of the secondary lead when the alignment device is retracted into the outer sheath of the catheter. This can present an atraumatic tip even where the nosecone is not constructed from a material having a soft durometer.

Referring now to FIGS. 4 and 5, in another embodiment, the alignment device 36 is attached to the outer sheath 12 and thereby remains immobile in relation to it. The inner sheath 28 is movably positioned at the rear of the alignment device 36 and again provides a pathway for the interconnection between the primary leads 30 and the electrical connector 18 (FIG. 1). In some embodiments the inner sheath 28 contains a guide-wire tube 49 that runs the entire length of the inner sheath. The guide-wire tube 49 is aligned to communicate with the central lumen 48 of the alignment device 36 at one end and with the guide-wire port 20 (FIG. 1) at the other end. The primary leads 30 may be continuous and run the entire length of the inner sheath 28 or they may be coupled to common leads as previously described. The primary leads 30 are secured to the front end 27 of the inner sheath 28, as for example with a potting material 50, so that the movement of the inner sheath 28 results in a corresponding movement of the primary leads 30 through the lumina 38 of the alignment device 36. In this embodiment, the primary leads 30 are not secured to the alignment device 36 and in essence are free-floating leads in the axial direction. The primary leads 30 travel through the alignment device 36 and exit through the distal orifice 14 as the front end of the inner sheath 28 is moved toward the rear 37 of the alignment device 36.

In the above embodiments, the primary leads 30 are formed, e. g., arced or bent, to move away from each other and thereby avoid contact. The "distal portion" of the primary leads 30 is the portion of the lead which extends from the front end of the alignment device 36 when the leads are fully extended through the distal orifice 14. It is preferred that the distal portions 42 are formed to move radially outward from each other relative to the axis of the alignment device 36 and form a symmetrical arrangement. This is shown in both the embodiments of FIG. 2a and FIG. 4a. The degree of arc or bend in the primary leads 30 may be any that is sufficient to radially expand the leads as they exit the outer sheath 12 through the distal orifice 14. It is essential that the degree of the arc or bend be sufficient to provide enough force so that the primary leads 30 expand through blood and the electrodes 34 come in apposition with the vein wall. The electrodes are preferably partially embedded in the vein wall to assure full contact. The rounded portion of the electrode is embedded into the vein wall to achieve full surface apposition so that the entire uninsulated surface area of the electrode is in contact with venous tissue for effective current distribution. The surface area of the electrodes in contact with the venous tissue preferably is sufficient to avoid a high current density which may lead to spot heating of the venous tissue. The heating effect is preferably distributed along a circumferential band of the vein. The apposed electrodes should be spaced no more than 4 or 5 millimeters from one another along the circumference of the vein. Thus, the electrode arrangement is related to the size or diameter of the vein being treated. Other properties of the primary leads 30, such as lead shape and insulation thickness, affect the push force of the lead and the degree of arc or bend must be adjusted to compensate for these factors. For example, in one configuration of the electrode device 24, a wire having a diameter of between 0.18 mm (0.007 in) and 0.28 mm (0.011 in) with a total insulation thickness of between 0.05 mm (0.002 in) to 0.13 mm (0.005 in) is arced or bent at an acute angle to provide sufficient apposition with the anatomical structure. It is to be understood that these dimensions are provided for illustrative purposes, and not by way of limitation.

Other techniques for expanding the leads outwardly once they have been extended from the working end of the catheter may be possible. For example, the leads may be straight but are mounted in the alignment device at an angle such that they are normally directed outward.

For increased appositional force, it is preferred that the primary leads 30 be strip-shaped, that is rectangular in cross section, with dimensions, for example, of a width from 0.76 mm (0.030 in.) to 1.0 mm (0.039 in) and a thickness of approximately 0.13 mm (0.005 in.). The rectangular cross section provides increased resistance to bending in the width dimension but allows bending more freely in the thickness dimension. This strip-shaped configuration of the primary leads 30 is shown in FIGS. 2, 2a, and 3 and provides for increased stability in the lateral direction while allowing the necessary bending in the radial direction. In FIGS. 2, 2a, and 3, each primary lead comprises a rectangular cross section mounted in relation to the catheter such that the thinner dimension of the rectangular cross section is aligned with the direction of expansion of the lead. The leads are less likely to bend sideways when expanded outward, and a uniform spacing between leads is more assured. Uniform spacing promotes uniform heating around the venous tissue which is in apposition with the electrodes at the distal ends of the leads.

The length of the distal portion of the leads 30 also affects the configuration of the electrode device 24. The maximum distance between two mutually opposed electrodes 34; i.e., the effective diameter of the electrode device 24, is affected by the bend degree and length of the distal portion 42. The longer the length of the distal portion 42 the greater the diameter of the electrode device 24. Accordingly, by changing the distal portion 42 length and arc or bend degree, the catheter 10 can be configured for use in differently sized anatomical structures.

Different numbers of leads 30, 31 can be employed with the catheter. The number of leads 30, 31 is limited by the diameter of the alignment device 36 and the number of lumina 36, 38, 47 that can be extruded through the alignment device. In a bipolar configuration, an even number of primary leads 30 are preferably available to form a number of oppositely charged electrode pairs. The electrodes in apposition with the anatomical structure should be maintained within a certain distance of each other. In a monopolar configuration, any number of commonly charged leads 30 can be present. In the monopolar mode, distribution of RF energy through the anatomical tissue is obtained by creating a return path for current through the tissue by providing a return device at a point external from the tissue, such as a large metal pad.

Now referring again to FIG. 1, an actuator 25 controls the extension of the electrode device 24 through the distal orifice 14. The actuator 25 may take the form of a switch, lever, threaded control knob, or other suitable mechanism, and is preferably one that can provide fine control over the movement of the outer sheath 12 or the inner sheath 28, as the case may be. In one embodiment of the invention, the actuator 25 (FIG. 1) interfaces with the outer sheath 12 (FIG. 2, 2a and 3) to move it back and forth relative to the inner sheath 28. In another embodiment the actuator 25 (FIG. 1) interfaces with the inner sheath 28 (FIGS. 4, 4a and 5) to move it back and forth relative to the outer sheath 12. The relative position between the outer sheath and inner sheath is thus controlled, but other control approaches may be used.

Referring again to FIGS. 2, 2a, 3, 4, 4a and 5, the catheter 10 includes a temperature sensor 26, such as a thermocouple. The temperature sensor 26 is mounted in place on an electrode 34 so that the sensor 26 is nearly or is substantially flush with the exposed surface of the electrode 34. The sensor 26 is shown in the drawings as protruding from the electrodes for clarity of illustration only. The sensor 26 senses the temperature of the portion of the anatomical tissue that is in apposition with the exposed electrode surface. Monitoring the temperature of the anatomical tissue provides a good indication of when shrinkage of the tissue is ready to begin. A temperature sensor 26 placed on the electrode facing the anatomical tissue provides an indication of when shrinkage occurs (70° C. or higher) and when significant amounts of heat-induced coagulum may begin to form on the electrodes. Therefore maintaining the temperature above 70 degrees Centigrade produces a therapeutic shrinkage of the anatomical structure. Application of the RF energy from the electrodes 34 is halted or reduced when the monitored temperature reaches or exceeds the specific temperature that was selected by the operator, typically the temperature at which anatomical tissue begins to cauterize. The temperature sensor 26 interfaces with the controller 23 (FIG. 1) through a pair of sensor leads 45 which preferably run through the auxiliary lumen 47 and then through the inner sheath 28. The signals from the temperature sensor 26 are provided to the controller 23 which controls the magnitude of RF energy supplied to the electrodes 34 in accordance with the selected temperature criteria and the monitored temperature. Other techniques such as impedance monitoring, and ultrasonic pulse echoing can be utilized in an automated system which shuts down or regulates the application of RF energy from the electrodes to the venous section when sufficient shrinkage of the vein is detected and to avoid overheating the vein. Impedance can be used to detect the onset of coagulum formation.

Referring now to FIGS. 6, 6a and 7a through 7c, in the operation of one embodiment of the catheter 10, the catheter is inserted into a hollow anatomical structure, such as a vein 52. The catheter is similar to the embodiment discussed in connection with FIGS. 2 and 3. The catheter 10 further includes an external sheath 60 through which a fluid can be delivered to the treatment site. In this embodiment, the fluid port (not shown) communicates with the interior of the external sheath 60, and fluid is delivered from between the external sheath 60 and the outer sheath 12. The external sheath 60 surrounds the outer sheath 12 to form a coaxial channel through which fluid may be flushed.

Fluoroscopy, ultrasound, an angioscope imaging technique, or other technique may be used to direct the specific placement of the catheter and confirm the position in the vein. The actuator (not shown) is then operated to shift the outer sheath relative to the inner sheath by either retracting the outer sheath 12 backward or advancing the inner sheath 28 forward to expose the leads 30, 31 through the distal orifice 14. As the leads 30, 31 exit the distal orifice 14, the primary leads 30 expand radially outward relative to the axis of the alignment device 36, while the secondary lead 31 remains substantially linear. The primary leads 30 continue to move outward until apposition with the vein wall 54 occurs and the outward movement of the primary leads 30 is impeded. The primary leads 30 contact the vein along a generally circumferential band of the vein wall 54. This outward movement of the primary leads 30 occurs in a substantially symmetrical fashion. As a result, the primary-lead electrodes 34 are substantially evenly spaced along the circumferential band of the vein wall 54. The central-lead electrode 35 is suspended within the vein 52 without contacting the vein wall 54.

When the electrodes 34 are positioned at the treatment site of the vein, the power supply 22 is activated to provide suitable RF energy. One suitable frequency is 510 kHz. One criterion used in selecting the frequency of the energy to be applied is the control desired over the spread, including the depth, of the thermal effect in the venous tissue. Another criterion is compatibility with filter circuits for eliminating RF noise from thermocouple signals.

In bipolar operation, the primary leads 30 are initially charged such that adjacent leads are oppositely charged while the secondary lead is electrically neutral. These multiple pairs of oppositely charged leads 30 form active electrode pairs to produce an RF field between them. Thus, discrete RF fields are set up along the circumferential band of the vein wall 54. These discrete fields form a symmetrical RF field pattern along the entire circumferential band of the vein wall 54, as adjacent electrodes 34 of opposite polarity produce RF fields between each other. A uniform temperature distribution can be achieved along the vein wall being treated.

The RF energy is converted within the adjacent venous tissue into heat, and this thermal effect causes the venous tissue to shrink, reducing the diameter of the vein. A uniform temperature distribution along the vein wall being treated avoids the formation of hot spots in the treatment area while promoting controlled uniform reduction in vein diameter. The thermal effect produces structural transfiguration of the collagen fibrils in the vein. The collagen fibrils shorten and thicken in cross-section in response to the heat from the thermal effect. As shown in FIG. 7a, the energy causes the vein wall 54 to collapse around the primary-lead electrodes 34. The wall 54 continues to collapse until further collapse is impeded by the electrodes 34. The electrodes are pressed farther and farther together by the shrinking vein wall 54 until they touch and at that point, further collapse or ligation of the wall 54 is impeded. Upon collapse of the vein wall 54 around the primary-lead electrodes 34, the polarity of the primary-lead electrodes is switched so that all primary-lead electrodes are commonly charged. The switching of polarity for the leads need not be instantaneous. The application of RF energy can be ceased, the polarity switched, and then RF energy is applied again at the switched polarity. The secondary-lead electrode 35 is then charged so that its polarity is opposite that of the primary-lead electrodes 34. The RF field is set up between the primary-lead electrodes 34 and the secondary-lead electrode 35.

The catheter 10 is then pulled back while energy is applied to the electrode device. As shown in FIG. 7b, while the catheter 10 is being pulled back, the primary-lead electrodes 34 remain in apposition with the vein wall 54 while the secondary-lead electrode 35 comes in contact with the portion of the vein wall previously collapsed by the primary-lead electrodes 34. Accordingly, RF energy passes through the vein wall 54 between the primary-lead electrodes 34 and the secondary-lead electrode 35 and the vein wall continues to collapse around the secondary-lead electrode 35 as the catheter 10 is being retracted. As shown in FIG. 7c, ligation in accordance with this method results in an occlusion along a length of the vein 52. A lengthy occlusion, as opposed to an acute occlusion, is stronger and less susceptible to recanalization.

A similar result is achieved when the catheter 10 having both primary and secondary leads is operated in a monopolar manner. In a monopolar operation, the secondary-lead electrode 35 remains neutral, while the primary leads 30 are commonly charged and act in conjunction with an independent electrical device, such as a large low-impedance return pad (not shown) placed in external contact with the body, to form a series of discrete RF fields. These RF fields are substantially evenly spaced around the circumference of the vein and travel along the axial length of the vein wall causing the vein wall to collapse around the primary-lead electrodes. Upon collapse of the vein wall, the secondary-lead electrode is charged to have the same polarity as that of the primary-lead electrodes. The electrode device is retracted and the vein wall collapses as described in the bipolar operation.

In either bipolar or monopolar operation the application of RF energy is substantially symmetrically distributed through the vein wall, regardless of the diameter of the vein 52. This symmetrical distribution of RF energy increases the predictability and uniformity of the shrinkage and the strength of the occlusion. Furthermore, the uniform distribution of energy allows for the application of RF energy for a short duration and thereby reduces or avoids the formation of heat-induced coagulum on the electrodes 34. The leads, including the non-convex outer portion of the electrode, are insulated to further prevent heating of the surrounding blood.

Fluid can be delivered before and during RF heating of the vein being treated through a coaxial channel formed between the external sheath 60 and the outer sheath 12. It is to be understood that another lumen can be formed in the catheter to deliver fluid to the treatment site. The delivered fluid displaces or exsanguinates blood from the vein so as to avoid heating and coagulation of blood. Fluid can continue to be delivered during RF treatment to prevent blood from circulating back to the treatment site. The delivery of a dielectric fluid increases the surrounding impedance so that RF energy is directed into the tissue of the vein wall.

Referring now to FIGS. 8, 8a, 9a and 9b, in the operation of an alternate embodiment of the catheter 10 that may be used with a guide wire 53. As in the previous embodiment, the catheter 10 is inserted into a hollow anatomical structure, such as a vein 52. The guide wire 53 is advanced past the point where energy application is desired. The catheter 10 is then inserted over the guide wire 53 by way of the central lumen 48 and the guide wire tube 49 (FIG. 4) and is advanced over the guide wire through the vein to the desired point. The guide wire 53 is typically pulled back or removed before RF energy is applied to the electrode device 24.

The actuator 25 (FIG. 1) is then manipulated to either retract the outer sheath 12 backward, or advance the inner sheath 28 forward to expose the leads 30 through the distal orifice 14. The leads 30 exit the distal orifice 14 and expand radially outward relative to the axis of the alignment device 36. The leads 30 continue to move outward until apposition with the vein wall 54 occurs. The leads 30 contact the vein along a generally circumferential band of the vein wall 54. This outward movement of the leads occurs in a substantially symmetrical fashion. As a result, the electrodes 34 are substantially evenly spaced along the circumferential band of the vein wall 54. Alternately, the electrodes can be spaced apart in a staggered fashion such that the electrodes do not lie along the same plane. For example, adjacent electrodes can extend different lengths from the catheter so that a smaller cross-sectional profile is achieved when the electrodes are collapsed toward one another.

When the electrodes 34 are positioned at the treatment site of the vein, the power supply 22 is activated to provide suitable RF energy to the electrodes 34 so that the catheter 10 operates in either a bipolar or monopolar manner as previously described. As shown in FIGS. 9a and 9b, the energy causes the vein wall 54 to collapse around the electrodes 34 causing the leads to substantially straighten and the electrodes to cluster around each other. The wall 54 continues to collapse until further collapse is impeded by the electrodes 34 (FIG. 9b). At this point the application of energy may cease. The electrodes can be configured to form a shape with a reduced profile when collapsed together. The electrodes can also be configured and insulated to continue applying RF energy after forming a reduced profile shape by the collapse of the vein wall. The catheter 10 can be pulled back to ligate the adjacent venous segment. If a temperature sensor 26 is included, the application of energy may cease prior to complete collapse if the temperature of the venous tissue rises above an acceptable level as defined by the controller 23.

Where the catheter includes a fluid delivery lumen (not shown), fluid can be delivered before and during RF heating of the vein being treated. The fluid can displace blood from the treatment area in the vein to avoid the coagulation of blood. The fluid can be a dielectric medium. The fluid can include an anticoagulant such as heparin which can chemically discourage the coagulation of blood at the treatment site.

After completing the procedure for a selected venous section, the actuator mechanism causes the primary leads to return to the interior of the outer sheath 12. Either the outer sheath or the inner sheath is moved to change the position of the two elements relative to one another. Once the leads 30 are within the outer sheath 12, the catheter 10 may be moved to another venous section where the ligation process is repeated. Upon treatment of all venous sites, the catheter 10 is removed from the vasculature. The access point of the vein is then sutured closed, or local pressure is applied until bleeding is controlled.

Another embodiment of the catheter is illustrated in FIG. 10. The inner member or sheath 28 is contained within the outer sheath 12. The inner sheath is preferably constructed from a flexible polymer such as polyimide, polyethylene, or nylon, and can travel the entire length of the catheter. The majority of the catheter should be flexible so as to navigate the tortuous paths of the venous system. A hypotube having a flared distal end 33 and a circular cross-sectional shape is attached over the distal end of the inner sheath 28. The hypotube is preferably no more than about two to three centimeters in length. The hypotube acts as part of the conductive secondary lead 31. An uninsulated conductive electrode sphere 35 is slipped over the hypotube. The flared distal end of the hypotube prevents the electrode sphere from moving beyond the distal end of the hypotube. The sphere is permanently affixed to the hypotube, such as by soldering the sphere both front and back on the hypotube. The majority or the entire surface of the spherical electrode 35 remains uninsulated. The remainder of the hypotube is preferably insulated so that the sphere-shaped distal end can act as the electrode. For example, the hypotube can be covered with an insulating material such as a coating of parylene. The interior lumen of the hypotube is lined by the inner sheath 28 which is attached to the flaired distal end of the hypotube by adhesive such as epoxy.

Surrounding the secondary lead 31 and sphere-shaped electrode 35 are a plurality of primary leads 30 which preferably have a flat rectangular strip shape and can act as arms. As illustrated in FIG. 11, the plurality of primary leads are preferably connected to common conductive rings 62. This configuration maintains the position of the plurality of primary leads, while reducing the number of internal electrical connections. The rings 62 are attached to the inner sheath 28. The position of the rings and the primary leads relative to the outer sheath follows that of the inner sheath. As earlier described, the hypotube of the secondary lead 31 is also attached to the inner sheath 28. Two separate conductive rings can be used so that the polarity of different primary leads can be controlled separately. For example, adjacent primary leads can be connected to one of the two separate conductive rings so that the adjacent leads can be switched to have either opposite polarities or the same polarity. The rings are preferable spaced closely together, but remain electrically isolated from one another along the inner sheath. Both the rings and the hypotube are coupled with the inner sheath, and the primary leads 30 that are connected to the rings move together with and secondary lead while remaining electrically isolated from one another. Epoxy or another suitable adhesive can be used to attach the rings to the inner sheath. The primary leads from the respective rings each alternate with each other along the circumference of the inner sheath. The insulation along the underside of the leads prevents an electrical short between the rings.

The ring and primary leads are attached together to act as cantilevers where the ring forms the base and the rectangular primary leads operate as the cantilever arms. The leads 30 are connected to the ring and are formed to have an arc or bend such that the leads act as arms which tend to spring outwardly away from the catheter and toward the surrounding venous tissue. Insulation along the underside of the leads and the rings prevents unintended electrical coupling between the leads and the opposing rings. Alternately, the leads are formed straight and connected to the ring at an angle, such that the leads tend to expand or spring radially outward from the ring. The angle at which the leads are attached to the ring should be sufficient to force the primary distal ends and electrodes 34 through blood and into apposition with the vein wall. Other properties of the primary leads 30, such as lead shape and insulation thickness, affect the push force of the lead and the degree of arc or bend must be adjusted to compensate for these factors. The rectangular cross section of the leads 30 can provide increased stability in the lateral direction while allowing the necessary bending in the radial direction. The leads 30 are less likely to bend sideways when expanded outward, and a uniform spacing between leads is more assured. Uniform spacing between the leads 30 and the distal ends promotes uniform heating around the vein by the electrodes 34.

The distal ends of the primary leads 30 are uninsulated to act as electrodes 34 having a spoon or hemispherical shape. The leads can be stamped to produce an integral shaped electrode at the distal end of the lead. The uninsulated outer portion of the distal end electrode 34 which is to come into apposition with the wall of the anatomical structure is preferably rounded and convex. The flattened or non-convex inner portion of the distal end is insulated to minimize any unintended thermal effect, such as on the surrounding blood in a vein. The distal end electrodes 34 are configured such that when the distal ends are forced toward the inner sheath 12, as shown in FIG. 10a, the distal ends combine to form a substantially spherical shape with a profile smaller than the profile for the spherical electrode 35 at the secondary distal end.

The outer sheath 12 can slide over and surround the primary and secondary leads 30, 31. The outer sheath 12 includes an orifice which is dimensioned to have approximately the same size as the spherical electrode 35 at the secondary distal end which functions as an electrode. A close or snug fit between the electrode 35 at the secondary distal end and the orifice of the outer sheath 12 is achieved. This configuration provides an atraumatic tip for the catheter. The electrode 35 secondary distal end is preferably slightly larger than the orifice. The inner diameter of the outer sheath 12 is approximately the same as the reduced profile of the combined primary distal end electrodes 34. The diameter of the reduced profile of the combined primary distal end electrodes 34 is preferably less than the inner diameter of the outer sheath.

A fluid port (not shown) can communicate with the interior of the outer sheath 12 so that fluid can be flushed between the outer sheath 12 and the inner sheath 28. Alternately, a fluid port can communicate with a central lumen 48 in the hypotube which can also accept a guide wire. As previously stated, the catheter 10 can be periodically flushed with saline which can prevent the buildup of biological fluid, such as blood, within the catheter 10. A guide wire can be introduced through the lumen 48 for use in guiding the catheter to the desired treatment site. As previously described, a fluid can be flushed or delivered though the lumen as well. If a central lumen is not desired, the lumen of the hypotube can be filled with solder.

Preferably, the primary leads 30 and the connecting rings are connected to a power source 22 such that the polarity of the leads may be switched as desired. This allows for the electrode device 24 to operate in either a bipolar or a monopolar configuration. When adjacent primary leads 30 have opposite polarity, a bipolar electrode operation is available. When the primary leads 30 are commonly charged a monopolar electrode operation is available in combination with a large return electrode pad placed in contact with the patient. When the primary leads 30 are commonly charged, and a secondary lead 31 has an opposite polarity, a bipolar electrode operation is available. More or fewer leads may be used. The number of leads can be dependent on the size or diameter of the hollow anatomical structure to be treated.

Although not shown, it is to be understood that the catheter 10 can include a temperature sensor, such as a thermocouple, mounted in place on the distal end or electrode 34 so that the sensor is substantially flush with the exposed surface of the electrode 34. The sensor senses the temperature of the portion of the anatomical tissue that is in apposition with the exposed electrode surface. Application of the RF energy from the electrodes 34 is halted or reduced when the monitored temperature reaches or exceeds the specific temperature that was selected by the operator, such as the temperature at which anatomical tissue begins to cauterize. Other techniques such as impedance monitoring, and ultrasonic pulse echoing can be utilized in an automated system which shuts down or regulates the application of RF energy from the electrodes to the venous section when sufficient shrinkage of the vein is detected and to avoid overheating the vein.

Figure 12:
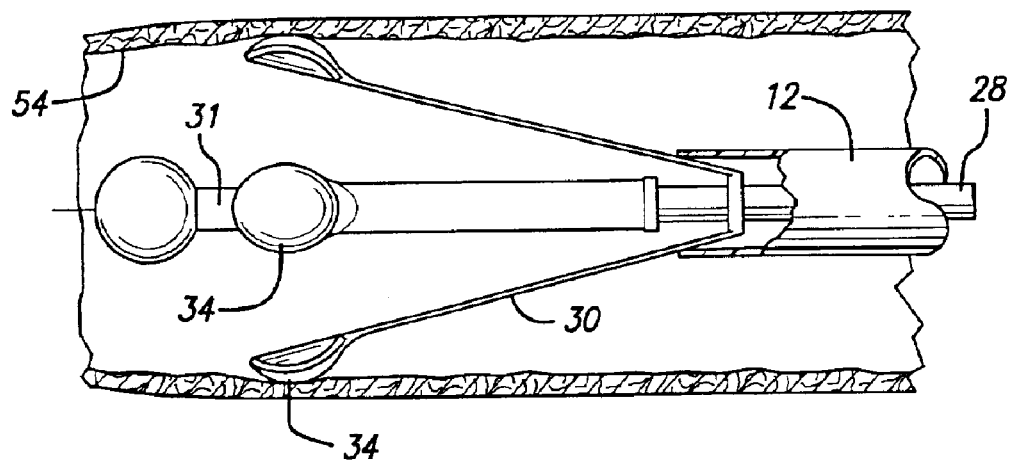
FIG. 12 is a cross-sectional view of an anatomical structure containing the catheter of FIG. 10 with the electrodes in apposition with the anatomical structure.
Figure 13:
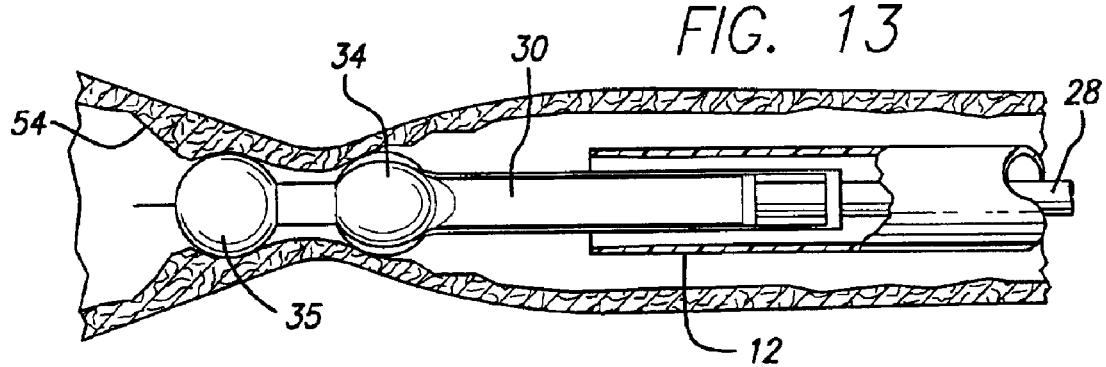
FIG. 13 is a cross-sectional view of the anatomical structure containing the catheter of FIG. 10 where the anatomical structure is being ligated by the application of energy from the electrodes.
Figure 14:
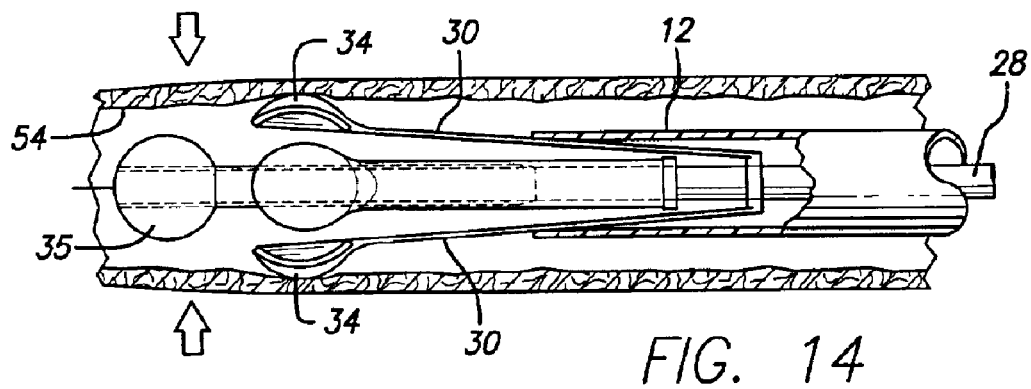
FIG. 14 is a cross-sectional view of an anatomical structure containing the catheter of FIG. 10 with the electrodes in apposition with the anatomical structure where external compression is being applied to reduce the diameter of the hollow structure before the application of energy from the electrodes to ligate the structure.

Referring now to FIGS. 12 through 14, in the operation of one embodiment of the catheter 10, the catheter is inserted into a hollow anatomical structure, such as a vein. Fluoroscopy, ultrasound, an angioscope imaging technique, or another technique may be used to direct and confirm the specific placement of the catheter in the vein. The actuator is then operated to retract the outer sheath 12 to expose the leads 30, 31. As the outer sheath no longer restrains the leads, the primary leads 30 move outward relative to the axis defined by the outer sheath, while the secondary lead 31 remains substantially linear along the axis defined by the outer sheath. The primary leads 30 continue to move outward until the distal end electrode 34 of the primary leads are placed in apposition with the vein wall 54 occurs and the outward movement of the primary leads 30 is impeded. The primary leads 30 contact the vein along a generally circumferential area of the vein wall 54. This outward movement of the primary leads 30 occurs in a substantially symmetrical fashion so that the primary distal end electrodes 34 are substantially evenly spaced. The central-lead electrode 35 is suspended within the vein without contacting the vein wall 54.

When the electrodes 34 are positioned at the treatment site of the vein, the power supply 22 is activated to provide suitable RF energy. In a bipolar operation, the primary leads 30 are initially charged such that adjacent leads are oppositely charged while the secondary lead is electrically neutral. These multiple pairs of oppositely charged leads 30 form active electrode pairs to produce an RF field between them, and form a symmetrical RF field pattern along a circumferential band of the vein wall to achieve a uniform temperature distribution along the vein wall being treated.

The RF energy produces a thermal effect which causes the venous tissue to shrink, reducing the diameter-of the vein. As shown in FIG. 13, the energy causes the vein wall 54 to collapse until further collapse is impeded by the electrodes 34. The electrodes are pressed closer together by the shrinking vein wall. The electrodes 34 are pressed together to assume a reduced profile shape which is sufficiently small so that the vein is effectively ligated. Upon collapse of the vein wall 54 around the primary-lead electrodes 34, the polarity of the primary-lead electrodes is switched so that all of the primary-lead electrodes are commonly charged. The secondary-lead electrode 35 is then charged so that its polarity is opposite that of the primary-lead electrodes 34. Where the primary electrodes 34 and the secondary electrode 35 are spaced sufficiently close together, when the vein wall collapses around the primary lead electrodes, the electrode at the distal end of the secondary lead can also come into contact with the a portion of the vein wall so that an RF field is created between the primary electrodes 34 and the secondary electrode 35.

The catheter 10 is pulled back to ensure apposition between the electrodes at the distal ends of the leads and the vein wall. When the catheter 10 is being pulled back, the primary-lead electrodes 34 remain in apposition with the vein wall 54 while the secondary-lead electrode 35 comes in contact with the portion of the vein wall previously collapsed by the primary-lead electrodes 34. RF energy passes through the venous tissue between the primary-lead electrodes 34 and the secondary-lead electrode 35. Ligation as the catheter is being retracted produces a lengthy occlusion which is stronger and less susceptible to recanalization than an acute point occlusion.

In a monopolar operation, the secondary-lead electrode 35 remains neutral, while the primary leads 30 are commonly charged and act in conjunction with an independent electrical device, such as a large low-impedance return pad (not shown) placed in external contact with the body, to form RF fields substantially evenly spaced around the circumference of the vein. The thermal effect produced by those RF fields along the axial length of the vein wall causes the vein wall to collapse around the primary-lead electrodes. Upon collapse of the vein wall, the secondary-lead electrode is charged to have the same polarity as that of the primary-lead electrodes. The electrode device-is retracted as described in the bipolar operation.

In either bipolar or monopolar operation the application of RF energy is substantially symmetrically distributed through the vein wall. As previously described, the electrodes should be spaced no more than 4 or 5 millimeters apart along the circumference of the vein, which defines the target vein diameter for a designed electrode catheter. Where the electrodes are substantially evenly spaced in a substantially symmetrical arrangement, and the spacing between the electrodes is maintained, a symmetrical distribution of RF energy increases the predictability and uniformity of the shrinkage and the strength of the occlusion.

As shown in FIG. 14, after the electrodes 34 come into apposition with the vein wall (FIG. 12), and before the energy is applied to ligate the vein (FIG. 13), an external tourniquet, such as an elastic compressive wrap or an inflatable bladder with a window transparent to ultrasound, is used to compress the anatomy, such as a leg, surrounding the structure to reduce the diameter of the vein. Although the compressive force being applied by the tourniquet may effectively ligate the vein, or otherwise occlude the vein by flattening the vein, for certain veins, this compressive force will not fully occlude the vein. A fixed diameter electrode catheter in this instance would not be effective. The electrodes 34 which are expanded outward by the formed leads 30 can accommodate this situation.

The reduction in vein diameter assists in pre-shaping the vein to prepare the vein to be molded to a ligated state. The use of an external tourniquet also exsanguinates the vein and blood is forced away from the treatment site. Coagulation of blood during treatment can be avoided by this procedure.

Energy is applied from the electrodes to the exsanguinated vein, and the vein is molded to a sufficiently reduced diameter to achieve ligation. The external tourniquet can remain in place to facilitate healing.

The catheter can be pulled back during the application of RF energy to ligate an extensive section of a vein. In doing so, instead of a single point where the diameter of the vein has been reduced, an extensive section of the vein has been painted by the RF energy from the catheter. Retracting the catheter in this manner produces a lengthy ***occlusion which is less susceptible to recanalization. The combined use of the primary and secondary electrodes can effectively produce a reduced diameter along an extensive length of the vein. The catheter can be moved while the tourniquet is compressing the vein, of after the tourniquet is removed.

Where the catheter includes a fluid delivery lumen, fluid can be delivered to the vein before RF energy is applied to the vein. The delivered fluid displaces blood from the treatment site to ensure that blood is not present at the treatment site, even after the tourniquet compresses the vein.

Where the tourniquet is an inflatable bladder with a window transparent to ultrasound, an ultrasound transducer is used to monitor the flattening or reduction of the vein diameter from the compressive force being applied by the inflating bladder. The window can be formed from polyurethane, or a stand-off of gel contained between a polyurethane pouch. A gel can be applied to the window to facilitate ultrasound imaging of the vein by the transducer. Ultrasound visualization through the window allows the operator to locate the desired venous treatment area, and to determine when the vein has been effectively ligated or occluded. Ultrasound visualization assists in monitoring any pre-shaping of the vein in preparation of being molded into a ligated state by the thermal effect produced by the RF energy from the electrodes.

After completing the procedure for a selected venous section, the actuator causes the leads 30 to return to the interior of the outer sheath 12. Once the leads 30 are within the outer sheath 12, the catheter 10 may be moved to another venous section where the ligation process is repeated.

In another embodiment, as illustrated in FIG. 15, a balloon 64 is located on the catheter, and can be inflated through ports 66 to occlude the vein. The inflated balloon obstructs blood flow and facilitates the infusion of a high-impedance fluid to the vein in order to reduce the occurrence of coagulation by directing the energy into the vein wall. The inflation of the balloon to occlude the vein before the application of energy can obviate the use of the tourniquet to occlude the vein. Furthermore, this also allows the vein to be occluded even for the deep veins where a compressive tourniquet may not be able to compress the vein to occlusion. It is to be understood that other mechanisms can be used to expand the diameter of the catheter to create an impermeable barrier that occludes the vein.

Fluid 61 can be delivered after inflation of the balloon 64 and before the RF heating of the vein being treated through a coaxial channel 62 formed between the external sheath 60 and the outer sheath 12. It is to be understood that another lumen can be formed in the catheter to deliver fluid to the treatment site. For example, the lumen through which the guide wire is passed may be used for the delivery of fluid. The delivered fluid displaces or exsanguinates the remaining blood from the treatment area of the vein so as to avoid heating and coagulation of blood. Fluid can continue to be delivered during RF treatment to prevent blood from circulating back to the treatment site. The delivery of a high-dielectric fluid increases the surrounding impedance so that RF energy is directed into the tissue of the vein wall. Less energy is used because the energy is directed to the target; i.e., the vein wall, rather than being dissipated in the blood. Therefore, the vein wall can reach the desired temperature more rapidly than in the case where energy is permitted to reach the blood, which has a cooling effect. Additionally, blood clotting is avoided with this approach, because the blood has been replaced with another fluid such as deionized water mixed with heparin to displace blood and prevent the formation of blood clots.

A partial cross-sectional view of this embodiment is shown in FIG. 16, where an inflation sheath 70 surrounds the external sheath 60 to provide a coaxial inflation lumen 72 for the balloon 64. The inflation lumen 72 is in fluid communication with the ports 66. Saline or any other suitable fluid can be used to inflate the balloon.

Figure 17:
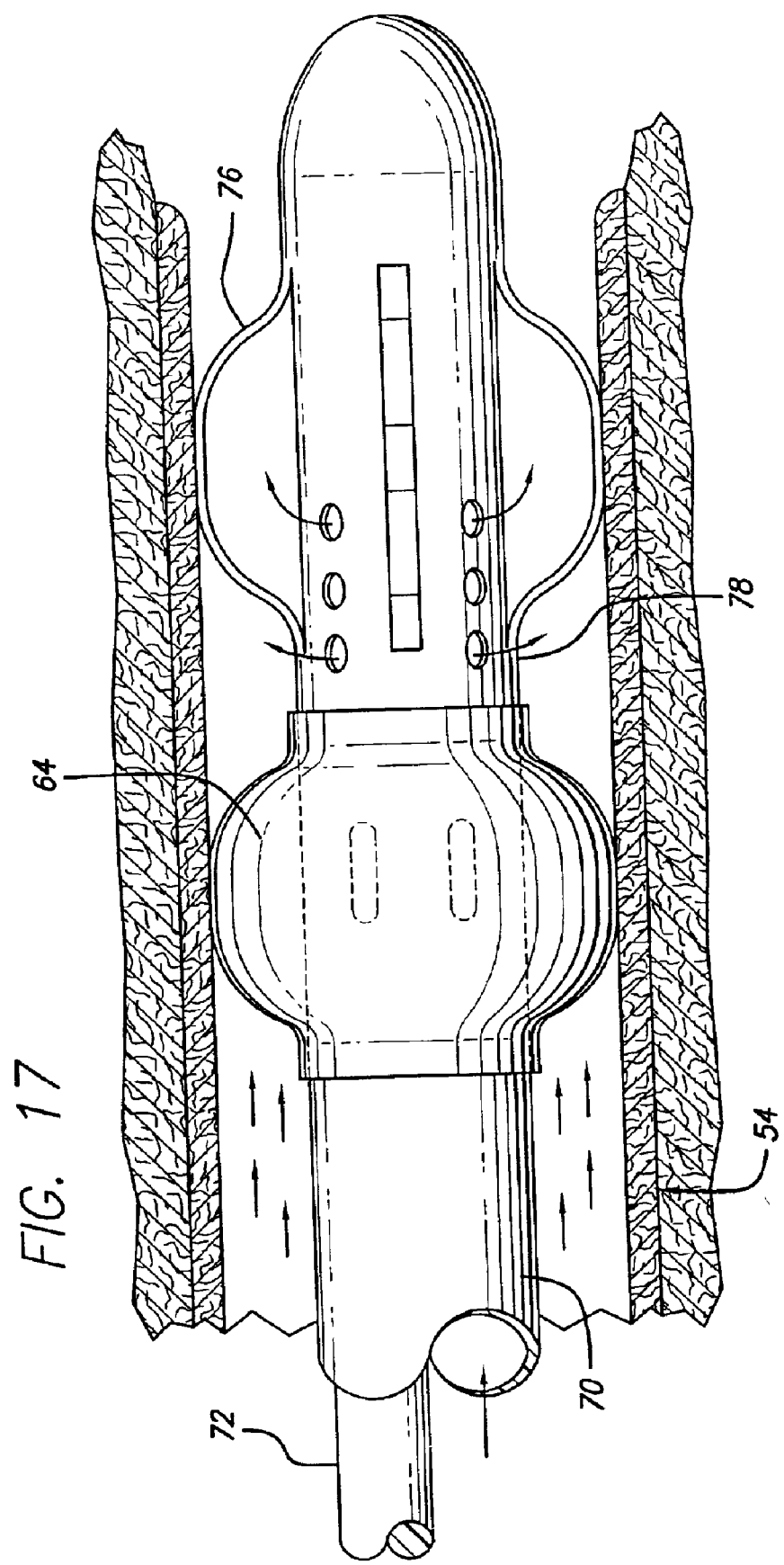
FIG. 17 is a cross-sectional view of an anatomical structure containing another embodiment of the catheter having a balloon and bowable arms with electrodes.

As shown in the FIG. 17, in one embodiment, the balloon 64 can be used in combination with bowable members or arms 76 having electrodes, where perfusion holes 78 are formed in the catheter between the balloon 64 and the bowable arms 76. The balloon 64 in this embodiment is inflated through a balloon inflation lumen 72. The use of bowable arms for treating veins is discussed in U.S. patent application Ser. No. 08/610,911, which is hereby incorporated by reference. The arms can be constructed so as to spring radially outward from the catheter, yet offer little resistance in moving back toward the catheter as the vein diameter is diminished to occlusion. An anticoagulant or saline or a high-impedance fluid can be introduced or flushed through the perfusion holes 78 in the catheter. As discussed earlier, the high-impedance fluid forces blood away from the venous treatment area and prevents the energy from being dissipated in a more conductive medium such as blood.

Figure 18:
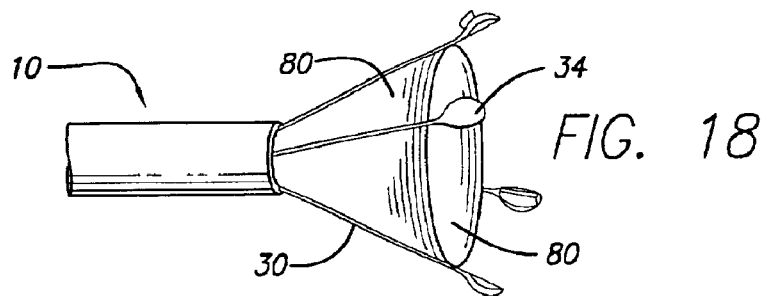
FIG. 18 is a side view of another embodiment of an electrode catheter having a covering spanning the splayed leads of the electrodes extended out the catheter.

As shown in FIG. 18, in another embodiment, a flexible covering 80 is wrapped around or inside the leads 30 of the electrodes 34 to prevent blood flow in the vein. The covering 80 spans the area between the splayed leads along the circumference of the catheter when the leads are extended out the opening, such that the webbed covering blocks blood flow within the vein. The covering may be thought of as webbing or an umbrella to keep blood on one side away from the electrodes. When the electrodes come into apposition with the vein wall, then the gap, if any, between the electrodes 34 and the covering 80 should be eliminated or otherwise minimized. The covering 80 should be impermeable to fluid. Suitable materials include PET and nylon. Elastomeric materials are also suitable as the leads will need to move close together as they are retracted, and interference with the movement of the leads as the vein diameter is reduced by the application of energy is preferably minimized. Although this embodiment is illustrated with only primary leads, it is to be understood that this embodiment is not so limited and that a secondary lead may be included with the catheter as well without affecting the use of the covering. As with the balloon disclosed earlier, the covering occludes the vein before the application of energy, such that the need for an external compressive tourniquet is not required to stop blood flow. Furthermore, this also allows the vein to be occluded even for the deep veins where a compressive tourniquet may not be able to compress the vein to occlusion. A high-impedance fluid such as deionized water, or an anti-coagulant such as heparin or saline, or both, or heparin with deionized water may be infused or flushed thorugh the perfusion holes 78 before the application of energy as well. The electrodes extend through the shaft lumen which also acts as a conduit for the fluid being flushed through the perfusion holes 78. A sclerosing fluid may also be delivered to the venous treatment site to enhance the ligation effect from the application of RF energy. The sclerosing fluid may be added in addition to, or in substitution of, the previously discussed fluids.

Figure 19:
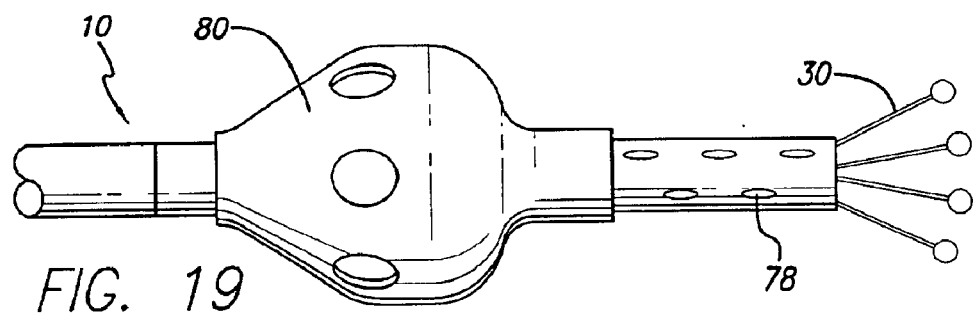
FIG. 19 is a side view of another embodiment of an electrode catheter having a balloon and a coaxial fluid channel.

In the embodiment shown in FIG. 19, a covering 80 having a parachute shape can be orientated so that blood becomes trapped by the concave portion of the covering and the volume of the blood maintains the deployment of the covering. In this example, the covering is a balloon having openings 84 which allow blood to gather in the balloon, and expand the balloon. The covering 80 can be permanently attached to the catheter shaft. The catheter can still be moved along the vein, even with the balloon in an inflated state.

Figure 20:
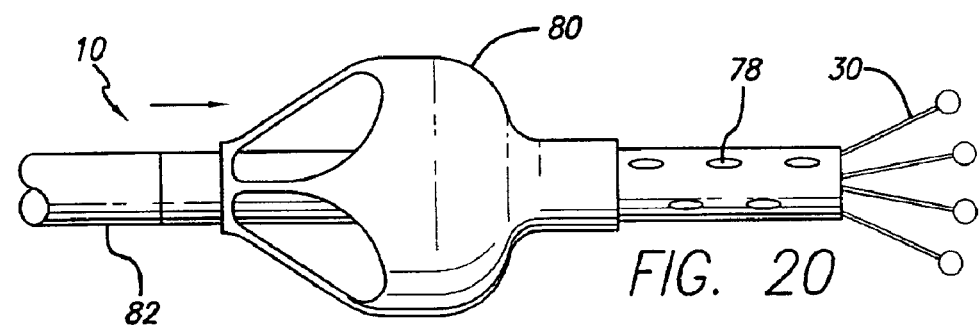
FIG. 20 is a side view of another embodiment of an electrode catheter having a balloon and a coaxial fluid channel.

In the embodiment shown in FIG. 20, the covering 80 is coupled to an outer cannula 82 surrounding the catheter shaft and connected to an actuation mechanism or lever. The outer cannula 82 can be slid along the longitudinal axis of the catheter to allow one end of the parachute covering 80 to be moved axially along the catheter shaft. During insertion of the catheter, the movable end of the covering is pulled away from the connecting end of the catheter to collapse the covering against the catheter. After the catheter is delivered to the venous treatment site, the cannula is slid toward the working end to deploy the covering which then fills with blood entering thorugh the openings 84, thereby occluding the vein. The covering expands as it fills with blood, and when the covering comes into contact with the vein wall, the vein is occluded. Fluid, as before, can be infused either through perfusion holes 78 or a coaxial channel.

Figure 21:
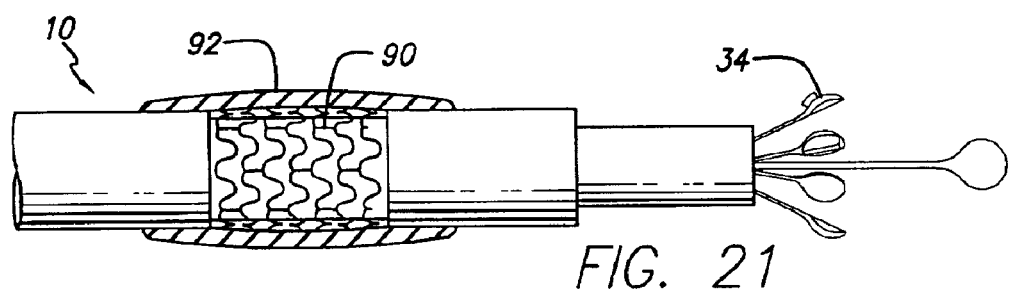
FIG. 21 is a partial cross-sectional side view of another embodiment of an electrode catheter having an expandable section.
Figure 22:
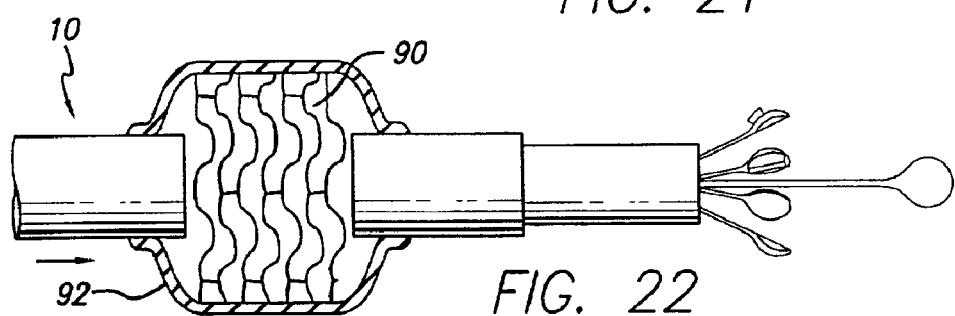
FIG. 22 is a partial cross-sectional side view of the embodiment of an electrode catheter of FIG. 21 in an expanded condition.

In the embodiment shown in the cross-sectional view of FIG. 21, the catheter 10 includes an expandable section having a skeleton 90 disposed along a portion of the working end of the catheter. The skeleton 90 is more flexible than the surrounding shaft of the catheter, and can be constructed from a metal or polymer braid. A flexible membrane 92 covers the skeleton 90, with the ends of the membrane attached to the shaft of the catheter adjacent the skeleton. The membrane is preferably constructed from an elastomeric material. As shown in FIG. 22, when the tip of the connecting end is moved toward the working end of the catheter, or vice versa, the skeleton 90 is deformed and forces the membrane 92 out into contact with the vein wall. This embodiment does not require a separate lumen to provide an inflation fluid to a balloon. The skeleton 90 is preferably resilient so that it returns to its original shape once the working end and connecting end are no longer being forced toward one another. Mechanisms for moving the connecting end toward the working end of the catheter for expanding the diameter of a catheter are also discussed in U.S. patent application Ser. No. 08/610,911, which has been incorporated by reference. Although the exapandable section may be controlled separately from the extension of the elecrodes, the expandable section can be controlled by the same mechanism which extends the electrodes away from the catheter.

The description of the component parts discussed above are for a catheter to be used in a vein ranging in size from 2 mm (0.08 in) to 13 mm (0.51 in) in diameter. It is to be understood that these dimensions do not limit the scope of the invention and are merely exemplary in nature. The dimensions of the component parts may be changed to configure a catheter 10 that may used in various-sized veins or other anatomical structures.

Although described above as positively charged, negatively charged, or as a positive conductor or negative conductor, these terms are used for purposes of illustration only. These terms are generally meant to refer to different electrode potentials and are not meant to indicate that any particular voltage is positive or negative. Furthermore, other types of energy such as light energy from fiber optics can be used to create a thermal effect in the hollow anatomical structure undergoing treatment.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. An apparatus for ligating a hollow anatomical structure, comprising:
    a catheter having a sheath, a working end, and an opening are located at the working end of the catheter;
    an inner member disposed within the sheath such that the inner member and the sheath are capable of being moved relative to one another;
    a plurality of leads, each lead having a distal end, the plurality of leads being coupled with the inner member such that the distal ends of the plurality of leads become extended out of the opening at the working end of the catheter when the inner member is moved relative to the sheath, each lead being formed to move the distal end away from a longitudinal axis defined by the sheath when the plurality of leads are extended out the opening, the distal end of each lead being capable of delivering energy to the anatomical structure;
    a flexible impermeable cover spanning the area between the leads, along the circumference of the catheter when the leads are extended out the opening, such that the cover blocks fluid flow within the hollow anatomical structure.

2. The apparatus of claim 1, further comprising at least one aperture formed in the working end of the catheter to allow the delivery of fluid therethrough.

3. The apparatus of claim 2, wherein the fluid is selected from the group consisting of a sclerosing fluid, an anticoagulant fluid, and saline.

4. The apparatus of claim 2, wherein the fluid has a high impedance.

5. The apparatus of claim 1, wherein leads have sufficient force to move into apposition with the wall of the hollow anatomical structure, and the leads do not have sufficient strength to prevent the reduction of the diameter of the hollow anatomical structure when energy is applied by the distal end of the leads.

6. The apparatus of claim 1, wherein the cover comprises an elastomeric material.

7. The apparatus of claim 1, wherein the cover is made of PET.

8. The apparatus of claim 1, wherein the cover is made of nylon.

9. The apparatus of claim 1, wherein the plurality of leads are primary leads, and wherein the apparatus further comprises at least one secondary lead.

10. The apparatus of claim 9, wherein the distal end of the secondary lead and the primary leads each further include an electrode.

11. The apparatus of claim 1, wherein the distal end of the leads each further include an electrode.

* * * * *

UNITED STATES PATENT AND TRADEMARK OFFICE
CERTIFICATE OF CORRECTION

PATENT NO. : 7,041,098 B2
APPLICATION NO. : 10/162057
DATED : May 9, 2006
INVENTOR(S) : Brian E. Farley et al.

It is certified that error appears in the above-identified patent and that said Letters Patent is hereby corrected as shown below:

<u>Title page</u>, Item 56, U.S. PATENT DOCUMENTS,
insert --4,564,011   1/1986   Goldman
         5,022,399   7/1991   Biegeleisen
         5,531,739   7/1996   Trelles--.
OTHER PUBLICATIONS, insert --Biegeleisen, K.; *Use Of The Venoscope For The Treatment Of Varicose Veins*, Phlebologie '89, pp. 419-22.--.

<u>Column 15</u>,
Line 50, delete "preferable" and insert --preferably--.
Line 54, delete "and" and insert --the--.

<u>Column 18</u>,
Line 9, delete "the a" and insert --the--.

<u>Column 19</u>,
Line 10, delete "***".

<u>Column 20</u>,
Line 66, delete "thorugh" and insert --through--.

<u>Column 21</u>,
Line 26, delete "thorugh" and insert --through--.
Line 53, delete "exapandable" and insert --expandable--.
Line 55, delete "elecrodes" and insert --electrodes--.

Signed and Sealed this

Thirtieth Day of January, 2007

JON W. DUDAS
*Director of the United States Patent and Trademark Office*